US012653525B2

(12) United States Patent
Almodovar

(10) Patent No.: US 12,653,525 B2
(45) Date of Patent: Jun. 16, 2026

(54) NEEDLE DRIVERS AND METHODS OF MANUFACTURE AND USE THEREOF

(71) Applicant: Ergosurgical Group Corp., San Juan, PR (US)

(72) Inventor: Luis Jose Almodovar, San Juan, PR (US)

(73) Assignee: Ergosurgical Group Corp., PR (US)

( * ) Notice: Subject to any disclaimer, the term of this patent is extended or adjusted under 35 U.S.C. 154(b) by 0 days.

(21) Appl. No.: 18/609,393

(22) Filed: Mar. 19, 2024

(65) Prior Publication Data

US 2024/0225635 A1 Jul. 11, 2024

Related U.S. Application Data

(62) Division of application No. 16/447,543, filed on Jun. 20, 2019, now Pat. No. 11,937,806.
(Continued)

(51) Int. Cl.
*A61B 17/04* (2006.01)
*A61B 17/29* (2006.01)

(52) U.S. Cl.
CPC ...... *A61B 17/0483* (2013.01); *A61B 17/0469* (2013.01); *A61B 2017/2903* (2013.01);
(Continued)

(58) Field of Classification Search
CPC .......... A61B 17/00234; A61B 17/0469; A61B 17/0483; A61B 17/0491; A61B 17/06061; A61B 17/062; A61B 17/29; A61B 2017/2825; A61B 2017/2903; A61B 2017/2912; A61B 2017/2926; A61B 2017/2927; A61B 2017/2929; A61B 2017/293; A61B 2017/2931; A61B 2017/2932; A61B 2017/2933;
(Continued)

(56) References Cited

U.S. PATENT DOCUMENTS

| | | | |
|---|---|---|---|
| 1,108,737 A | 8/1914 | Gajdos | |
| 2,601,564 A | 6/1952 | Smith | |
(Continued)

FOREIGN PATENT DOCUMENTS

| | | | | |
|---|---|---|---|---|
| EP | | 3034019 A1 * | 6/2016 | ............. A61B 17/29 |
| WO | WO2009039506 | | 3/2009 | |
(Continued)

OTHER PUBLICATIONS

EP3034019 (Year: 2014).*
(Continued)

*Primary Examiner* — Kankindi Rwego
(74) *Attorney, Agent, or Firm* — Dentons US LLP

(57) ABSTRACT

A needle driver can include a first jaw hosting a first shaft and a second jaw hosting a second shaft. The first shaft hosts a first roller and a first set of teeth. The second shaft hosts a second roller and a second set of teeth. The second jaw moves relative to the first jaw between an open position and a closed position. The first set of teeth meshes with the second set of teeth when the second jaw is in the closed position such that (a) the first set of teeth can drive the second set of teeth and (b) the first roller and the second roller can drive a needle therebetween when the first set of teeth drives the second set of teeth.

23 Claims, 20 Drawing Sheets

Related U.S. Application Data

(60) Provisional application No. 62/687,752, filed on Jun. 20, 2018.

(52) U.S. Cl.
CPC ................ *A61B 2017/2912* (2013.01); *A61B 2017/2932* (2013.01)

(58) Field of Classification Search
CPC .... A61B 2017/2934; A61B 2017/2936; A61B 2017/2938; A61B 2017/2939; A61B 2017/294; A61B 2017/2941; A61B 2017/2943; A61B 2017/2944; A61B 2017/2945; A61B 2017/00867; A61B 34/30; A61B 34/70; A61B 34/71; A61B 34/74
USPC ....... 606/139, 144, 145, 146, 147, 148, 205, 606/206, 207, 208, 209
See application file for complete search history.

(56) References Cited

U.S. PATENT DOCUMENTS

| | | | |
|---|---|---|---|
| 3,168,097 | A | 2/1965 | Earico |
| 4,287,890 | A * | 9/1981 | Fogarty .................. A61B 17/00 |
| | | | 294/118 |
| 4,452,244 | A * | 6/1984 | Chin ........................ A61M 1/83 |
| | | | 606/209 |
| 4,580,567 | A | 4/1986 | Schweitzer et al. |
| 4,635,638 | A * | 1/1987 | Weintraub ......... A61B 17/0469 |
| | | | 269/140 |
| 4,642,106 | A * | 2/1987 | Downey ................... A61F 5/44 |
| | | | 600/573 |
| 4,763,669 | A | 8/1988 | Jaeger |
| 5,496,334 | A | 3/1996 | Klundt et al. |
| 5,501,690 | A | 3/1996 | Measamer et al. |
| 5,545,148 | A * | 8/1996 | Wurster ............. A61B 17/0469 |
| | | | 604/223 |
| 5,582,617 | A | 12/1996 | Klieman et al. |
| 5,628,757 | A | 5/1997 | Hasson |
| 5,722,990 | A * | 3/1998 | Sugarbaker ...... A61B 17/00234 |
| | | | 606/1 |
| 5,759,188 | A | 6/1998 | Yoon |
| 5,843,100 | A | 12/1998 | Meade |
| 5,860,992 | A | 1/1999 | Daniel et al. |
| 5,891,159 | A | 4/1999 | Sherman et al. |
| 5,897,563 | A | 4/1999 | Yoon et al. |
| 5,954,731 | A | 9/1999 | Yoon |
| 5,954,733 | A | 9/1999 | Yoon |
| 5,957,937 | A | 9/1999 | Yoon |
| 5,984,932 | A | 11/1999 | Yoon |
| 5,993,466 | A | 11/1999 | Yoon |
| 5,993,467 | A | 11/1999 | Yoon |
| 6,004,332 | A | 12/1999 | Yoon et al. |
| 6,071,289 | A | 6/2000 | Stefanchik et al. |
| 6,086,601 | A | 7/2000 | Yoon |
| 6,126,665 | A | 10/2000 | Yoon |
| 6,143,005 | A | 11/2000 | Yoon et al. |
| 6,159,224 | A | 12/2000 | Yoon |
| 6,224,614 | B1 | 5/2001 | Yoon |
| 7,331,970 | B2 | 2/2008 | Almodovar |
| 7,588,583 | B2 | 9/2009 | Hamilton et al. |
| 8,021,376 | B2 | 9/2011 | Takemoto et al. |
| 8,252,007 | B2 | 8/2012 | Hamilton et al. |
| 8,317,805 | B2 | 11/2012 | Hamilton et al. |
| 8,603,113 | B2 | 12/2013 | Hamilton et al. |
| 8,696,690 | B2 | 4/2014 | Almodovar |
| 9,192,376 | B2 | 11/2015 | Almodovar |
| 9,730,689 | B2 | 8/2017 | Almodovar |
| 10,786,245 | B2 | 9/2020 | Almodovar |
| 2003/0181924 | A1 | 9/2003 | Yamamoto et al. |
| 2006/0020272 | A1 | 1/2006 | Gildenberg |
| 2006/0064116 | A1 | 3/2006 | Allen et al. |
| 2006/0282096 | A1 | 12/2006 | Papa et al. |
| 2007/0016287 | A1 | 1/2007 | Cartledge et al. |
| 2007/0021755 | A1 | 1/2007 | Almodovar |
| 2007/0060930 | A1 * | 3/2007 | Hamilton ........... A61B 17/2841 |
| | | | 606/144 |
| 2007/0135913 | A1 | 6/2007 | Moaddeb et al. |
| 2007/0203507 | A1 | 8/2007 | McLaughlin et al. |
| 2008/0004604 | A1 | 1/2008 | Hartwick |
| 2008/0071295 | A1 | 3/2008 | Baxter et al. |
| 2008/0103511 | A1 | 5/2008 | Almodovar |
| 2008/0262609 | A1 | 10/2008 | Gross et al. |
| 2009/0240263 | A1 | 9/2009 | Kawai et al. |
| 2009/0326559 | A1 | 12/2009 | Almodovar |
| 2010/0042116 | A1 | 2/2010 | Chui et al. |
| 2010/0191259 | A1 | 7/2010 | Suzuki et al. |
| 2011/0054499 | A1 | 3/2011 | Almodovar |
| 2011/0152891 | A1 | 6/2011 | McLawhorn et al. |
| 2011/0270281 | A1 | 11/2011 | Malkowski |
| 2012/0150199 | A1 | 6/2012 | Woodard, Jr. et al. |
| 2012/0239011 | A1 | 9/2012 | Hyodo et al. |
| 2013/0253548 | A1 * | 9/2013 | Harrison ................ A61B 17/11 |
| | | | 606/153 |
| 2014/0222036 | A1 | 8/2014 | Hamilton et al. |
| 2014/0277405 | A1 | 9/2014 | Wilson et al. |
| 2014/0296417 | A1 | 10/2014 | Hans et al. |
| 2014/0309683 | A1 * | 10/2014 | Bagwell ............. A61B 18/1492 |
| | | | 606/207 |
| 2015/0081014 | A1 | 3/2015 | Gross et al. |
| 2015/0127025 | A1 | 5/2015 | Hamilton et al. |
| 2016/0074032 | A1 * | 3/2016 | Almodovar .......... A61B 17/062 |
| | | | 606/147 |
| 2017/0119416 | A1 | 5/2017 | Sajid |
| 2018/0116653 | A1 | 5/2018 | Almodovar |
| 2018/0236164 | A1 * | 8/2018 | Song ..................... A61M 5/158 |
| 2019/0388087 | A1 | 12/2019 | Almodovar |
| 2021/0100549 | A1 | 4/2021 | Almodovar |

FOREIGN PATENT DOCUMENTS

| | | |
|---|---|---|
| WO | WO2011029105 | 3/2011 |
| WO | WO2012057807 | 5/2012 |
| WO | WO2015074066 | 5/2015 |
| WO | WO2016011594 | 1/2016 |
| WO | WO2017091680 | 6/2017 |
| WO | WO2019246437 | 12/2019 |

OTHER PUBLICATIONS

Japan Office Action dated Mar. 8, 2023 in related serial No. 2021-520280 filed Jun. 20, 2019 (23 pages).

Fontanelli et al., A New Laparoscopic Tool with In-Hand Rolling Capabilities for Needle Reorientation, IEE Robotics and Automation Letters, Jan. 2018 (8 pages).

International Search Report and Written Opinion dated Mar. 6, 2012 in related International Application No. PCT/US2010/055370 filed Nov. 4, 2010 (10 pages).

International Search Report and Written Opinion dated Jan. 10, 2019 in related International Application No. PCT/US2019/038308 filed Jun. 20, 2019 (5 pages).

International Search Report and Written Opinion dated Mar. 10, 2011 in related International Application No. PCT/US2010/054651 filed Oct. 29, 2020 (7 pages).

International Search Report and Written Opinion dated May 14, 2019 in related International Application No. PCT/US2019/012199 filed Jan. 3, 2019 (14 pages).

International Search Report and Written Opinion dated Feb. 21, 2017 in related International Application No. PCT/US2016/063513 filed Nov. 23, 2016 (9 pages).

China Office Action dated Dec. 21, 2023 in related application 2019800546204 filed Dec. 21, 2023 (9 pages).

China Office Action dated Aug. 1, 2024 in related application 2019800546204 filed Jun. 20, 2019 (6 pages).

Europe Office Action dated Aug. 28, 2024 in related application 19737381.4 filed Jun. 20, 2019 (8 pages).

(56)         References Cited

OTHER PUBLICATIONS

Europe Office Action dated Aug. 13, 2025 in related application
19737381.4 filed Jun. 20, 2019 (7 pages).

* cited by examiner

Closed Position

116

108

104

144

112

106

200

204

208

218

202

206

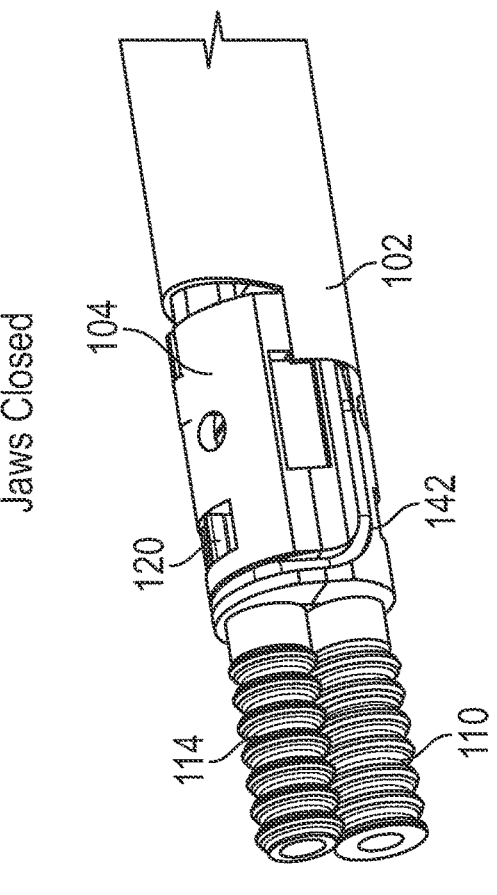
Jaws Closed
FIG. 14
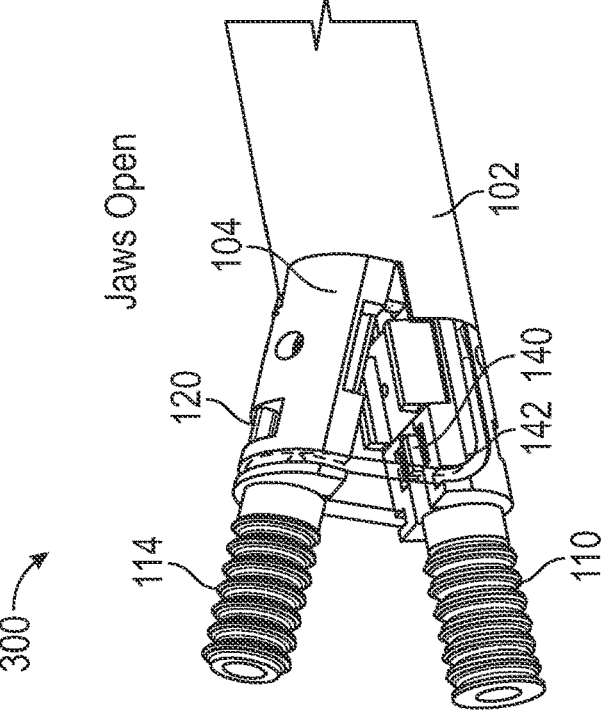
Jaws Open

400

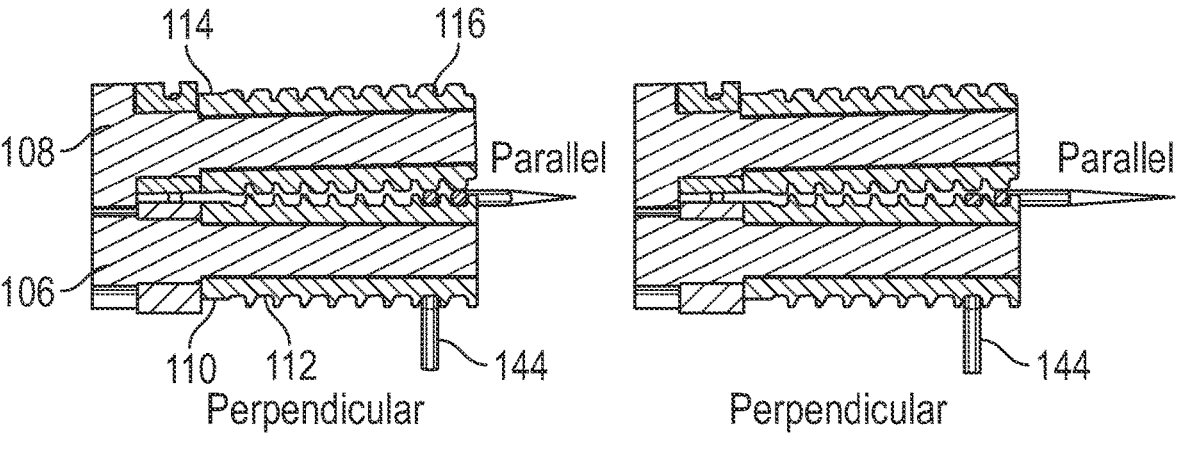
FIG. 19                    FIG. 20
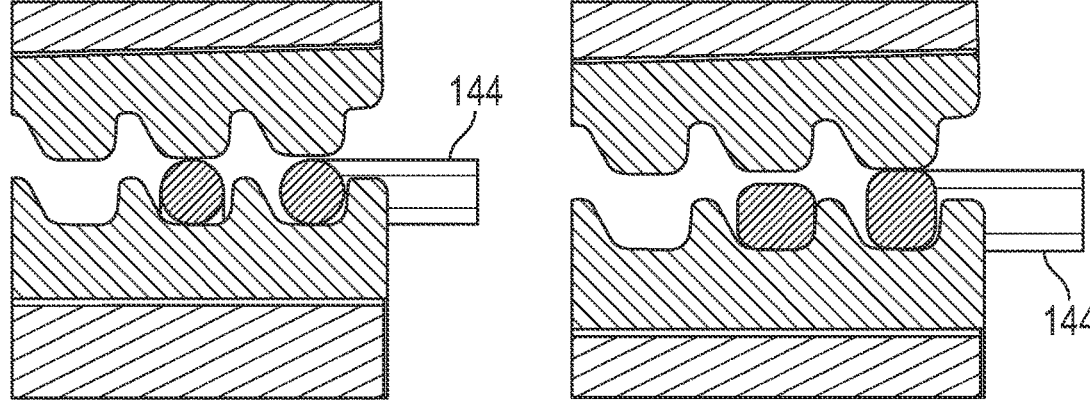
FIG. 21

800
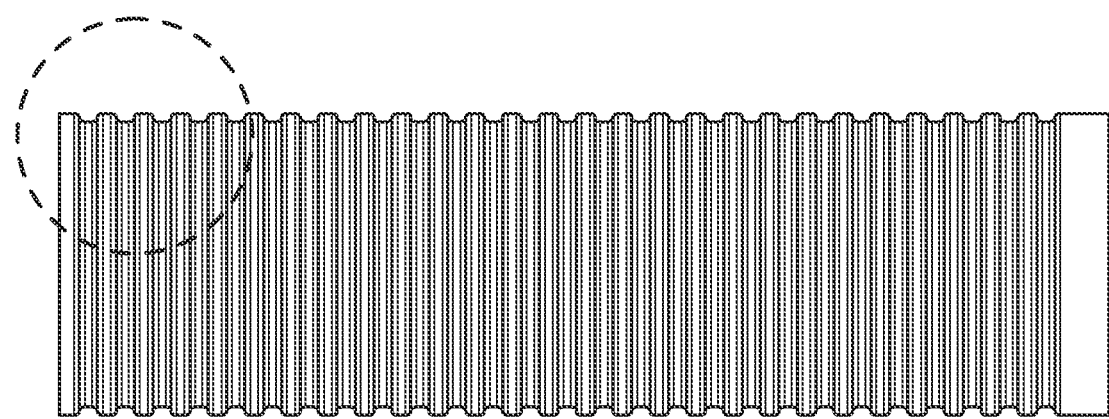
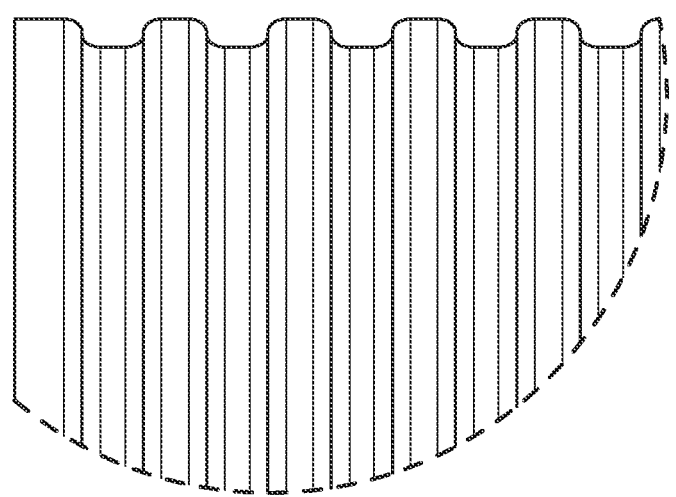
FIG. 31

NEEDLE DRIVERS AND METHODS OF MANUFACTURE AND USE THEREOF

CROSS-REFERENCE TO RELATED APPLICATIONS

This application is a Divisional of U.S. patent application Ser. No. 16/447,543 filed 20 Jun. 2019, now U.S. Pat. No. 11,937,806 issued 26 Mar. 2024, which claims the benefit of U.S. Provisional Patent Application No. 62/687,752 filed 20 Jun. 2018, each of which is herein incorporated by reference for all purposes.

TECHNICAL FIELD

Generally, this disclosure relates to surgical instruments. More particularly, this disclosure relates to needle drivers.

BACKGROUND

A surgeon operating on a tissue within a patient may need to suture through the tissue, grasp the tissue, or dissect the tissue. However, these actions require a set of different surgical instruments, which can be expensive to obtain, incompatible with each other, laborious to disinfect, non-ergonomic, bulky, or time consuming to insert into the patient or to withdraw from within the patient. Additionally, if suturing requires a needle and the needle varies in size, then the set of different surgical instruments may need to contain a needle specific driver, which can be expensive to obtain, incompatible with other members of the set of different surgical instruments, laborious to disinfect, non-ergonomic, bulky, or time consuming to insert into the patient or to withdraw from within the patient. Moreover, if the needle needs to be driven into the tissue at various angles, then the set of different surgical instruments may need to contain an angle specific needle driver, which can be expensive to obtain, incompatible with other members of the set of different surgical instruments, laborious to disinfect, non-ergonomic, bulky, or time consuming to insert into the patient or to withdraw from within the patient. Also, if the surgeon is not right handed or ambidextrous, then some member of the set of different surgical instruments may need to be configured for left-handed use, which may be expensive to locate, non-existent, or incompatible with some right-handed surgical instruments if corresponding left-handed surgical instruments are not readily available.

Laparoscopic surgery can be challenging to master and requires a different set of skills from open surgery. For example, during the laparoscopic surgery, the surgeon has a limited range of motion, enters the patient through a small incision in the patient, and uses a set of laparoscopic surgical instruments with limited visibility in a crowded surgical area within the patient. Moreover, some member of the set of laparoscopic surgical instruments can have some endpoints that move in directions opposite to movements of the surgeon due to a presence of a pivot point, thereby making at least some surgical movements non-intuitive or difficult to learn. Additionally, at least some visualization of laparoscopic procedures occurs using a two-dimensional display at a distance with a limited haptic feedback, thereby limiting at least some depth perception and cumulatively complicating the laparoscopic procedures.

Laparoscopic suturing and knot tying can be laborious and time consuming, requiring coordination of multiple steps, significant concentration and effort, and thereby presenting a challenge for at least some laparoscopic surgeons.

This may be so because during the laparoscopic surgery, at least some surgeons have difficulty assessing depth and three-dimensional orientation to place the set of laparoscopic surgical instruments. Those surgeons can be challenged by limited visibility (visualization occurs using a two-dimensional display at a distance), limited range of motion and haptic feedback, and some tool endpoints moving in directions opposite to that of the surgeon.

Extended surgical time needed to perform laparoscopic suturing and knot tying can also be problematic. Numerous studies have shown an association between longer duration of anesthesia and negative outcomes, postoperative nausea and vomiting, thromboembolism, postoperative infection, postoperative core hypothermia, postoperative cardiopulmonary complications, and death in cosmetic surgery. Analysis of a large corpus of surgical operations has found that operative duration is independently associated with increased risk-adjusted infection complications and length of stay.

SUMMARY

In an embodiment, a needle driver comprises a first jaw hosting a first shaft, wherein the first shaft hosts a first roller and a first set of teeth; and a second jaw hosting a second shaft, wherein the second shaft hosts a second roller and a second set of teeth, wherein the second jaw moves relative to the first jaw between an open position and a closed position, wherein the first set of teeth meshes with the second set of teeth when the second jaw is in the closed position such that (a) the first set of teeth can drive the second set of teeth and (b) the first roller and the second roller can drive a needle therebetween when the first set of teeth drives the second set of teeth.

In an embodiment, a method comprises causing a device to be inserted into a first object, wherein the device includes a first jaw hosting a first shaft and a second jaw hosting a second shaft, wherein the first shaft hosts a first roller and a first set of teeth, wherein the second shaft hosts a second roller and a second set of teeth, wherein the second jaw moves relative to the first jaw between an open position and a closed position, wherein the first set of teeth meshes with the second set of teeth when the second jaw is in the closed position such that (a) the first set of teeth can drive the second set of teeth and (b) the first roller and the second roller can drive a needle therebetween when the first set of teeth drives the second set of teeth; and causing the first roller and the second roller to grasp a second object therebetween within the first object when the second jaw is in the closed position.

In an embodiment, a method comprises causing a device to be inserted into a first object, wherein the device includes a first jaw hosting a first shaft and a second jaw hosting a second shaft, wherein the first shaft hosts a first roller and a first set of teeth, wherein the second shaft hosts a second roller and a second set of teeth, wherein the second jaw moves relative to the first jaw between an open position and a closed position, wherein the first set of teeth meshes with the second set of teeth when the second jaw is in the closed position such that (a) the first set of teeth can drive the second set of teeth and (b) the first roller and the second roller can drive a needle therebetween when the first set of teeth drives the second set of teeth; and causing the first roller and the second roller to manipulate a second object within the first object when the second jaw is in the closed position.

3

In an embodiment, a method comprises causing a device to be inserted into a first object, wherein the device includes a first jaw hosting a first shaft and a second jaw hosting a second shaft, wherein the first shaft hosts a first roller and a first set of teeth, wherein the second shaft hosts a second roller and a second set of teeth, wherein the second jaw moves relative to the first jaw between an open position and a closed position, wherein the first set of teeth meshes with the second set of teeth when the second jaw is in the closed position such that (a) the first set of teeth can drive the second set of teeth and (b) the first roller and the second roller can drive a needle therebetween when the first set of teeth drives the second set of teeth; and causing the first roller and the second roller to dissect a second object within the first object when the second jaw is in the closed position.

In an embodiment, a method comprises causing a device to be inserted into a first object, wherein the device includes a first jaw hosting a first shaft and a second jaw hosting a second shaft, wherein the first shaft hosts a first roller and a first set of teeth, wherein the second shaft hosts a second roller and a second set of teeth, wherein the second jaw moves relative to the first jaw between an open position and a closed position, wherein the first set of teeth meshes with the second set of teeth when the second jaw is in the closed position such that (a) the first set of teeth can drive the second set of teeth and (b) the first roller and the second roller can drive a needle therebetween when the first set of teeth drives the second set of teeth; and causing the first roller and the second roller to isolate a second object within the first object when the second jaw is in the closed position.

In an embodiment, a method comprises causing a device to be inserted into a first object, wherein the device includes a first jaw hosting a first shaft and a second jaw hosting a second shaft, wherein the first shaft hosts a first roller and a first set of teeth, wherein the second shaft hosts a second roller and a second set of teeth, wherein the second jaw moves relative to the first jaw between an open position and a closed position, wherein the first set of teeth meshes with the second set of teeth when the second jaw is in the closed position such that (a) the first set of teeth can drive the second set of teeth and (b) the first roller and the second roller can drive a needle therebetween when the first set of teeth drives the second set of teeth; and causing the first roller and the second roller to separate a second object within the first object when the second jaw is in the closed position.

In an embodiment, a needle driver comprises a first jaw hosting a first shaft, wherein the first shaft hosts a first roller and a first set of teeth; and a second jaw hosting a second shaft, wherein the second shaft hosts a second roller including a cylindrical portion, wherein the second jaw moves relative to the first jaw between an open position and a closed position, wherein the first set of teeth abuts the cylindrical portion when the second jaw is in the closed position such that (a) the cylindrical portion can drive the first set of teeth, and (b) the first roller and the second roller can drive a needle therebetween when the cylindrical portion drives the first set of teeth.

In an embodiment, a method comprises causing a device to be inserted into a first object, wherein the device includes a first jaw hosting a first shaft and a second jaw hosting a second shaft, wherein the first shaft hosts a first roller and a first set of teeth, wherein the second shaft hosts a second roller including a cylindrical portion, wherein the second jaw moves relative to the first jaw between an open position and a closed position, wherein the first set of teeth abuts the cylindrical portion when the second jaw is in the closed position such that (a) the cylindrical portion can drive the first set of teeth, and (b) the first roller and the second roller can drive a needle therebetween when the cylindrical portion drives the first set of teeth; and causing the first roller and the second roller to at least one of grasp, separate, manipulate, dissect, or isolate a second object within the first object when the second jaw is in the closed position.

In an embodiment, when the second jaw is in the closed position, the first roller and the second roller grasp a needle in a plane of orientation. In an embodiment, the plane of orientation is perpendicular to the axis of the first shaft. In an embodiment, the plane of orientation is parallel to the axis of the first shaft. In an embodiment, the plane of orientation is at an angle to the axis of the first shaft.

DESCRIPTION OF DRAWINGS

FIG. 14 shows a front view of an embodiment of a needle driver hosting a line according to this disclosure.

FIG. 19 shows a diagram of an embodiment of a side profile of a pair of rollers engaging an arcuate needle according to this disclosure.

FIG. 20 shows a diagram of an embodiment of a side profile of a pair of rollers engaging an arcuate needle according to this disclosure.

FIG. 21 shows a pair of diagrams of a pair of embodiments of a pair of side profiles of a pair of rollers engaging a pair of arcuate needles of a pair of different sizes according to this disclosure.

FIG. 31 shows a diagram of a side profile of a roller according to this disclosure.

DETAILED DESCRIPTION OF PREFERRED EMBODIMENTS

Figure 1:
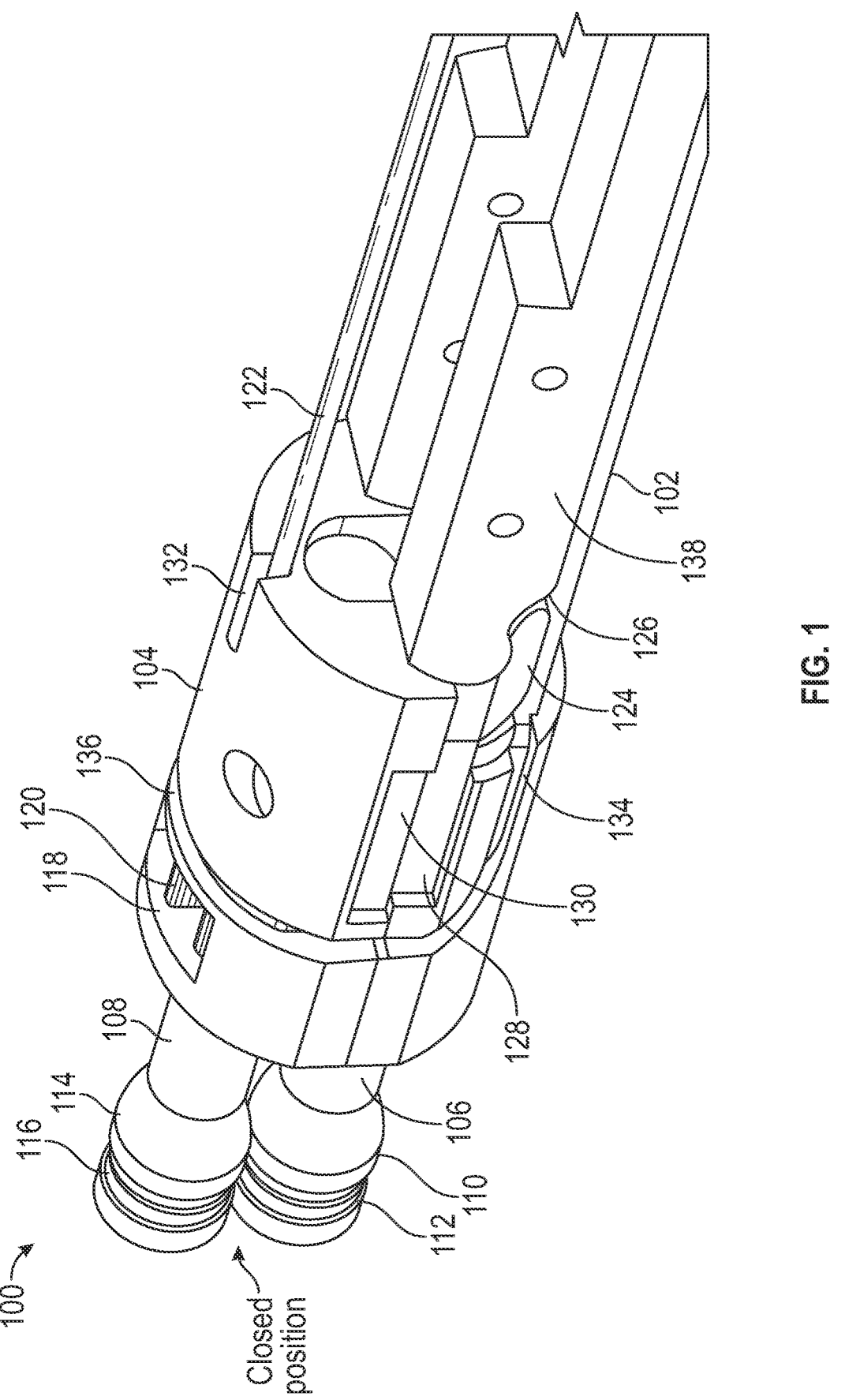
FIG. 1 shows a rear view of an embodiment of a needle driver in a closed position according to this disclosure.

Generally, this disclosure discloses various needle drivers and methods of manufacture and use thereof. The needle drivers can include a plurality of rollers that can move between a closed position and an open position. The rollers can rotationally drive a needle therebetween when the rollers are in the closed position. Likewise, the rollers can be used to grasp an object (e.g., animate, inanimate, tissue, instrument, implantable) when the rollers are in the closed position or in the open position or act (e.g., manipulate, dissect, isolate, separate, intervene, mount, drop, move, drag) with the object when the rollers are in the closed position or in the open position. For example, the object, when animate, can include a tissue, an organ, a body part, whether of human or animal, or others. For example, the tissue can be a muscle tissue, a bone tissue, a nerve tissue, an organ tissue, or others. For example, the object, when inanimate, can include a medical device, a prosthesis, an implantable, a machine, a surgical instrument, or others. The closed position can be a clamping position. Note that this disclosure may be embodied in many different forms and should not be construed as necessarily being limited to various embodiments disclosed herein. Rather, these embodiments are provided so that this disclosure is thorough and complete, and fully conveys various concepts of this disclosure to skilled artisans.

Note that various terminology used herein can imply direct or indirect, full or partial, temporary or permanent, action or inaction. For example, when an element is referred to as being "on," "connected," or "coupled" to another element, then the element can be directly on, connected, or coupled to another element or intervening elements can be present, including indirect or direct variants. In contrast, when an element is referred to as being "directly connected" or "directly coupled" to another element, then there are no intervening elements present.

As used herein, various singular forms "a," "an" and "the" are intended to include various plural forms as well, unless specific context clearly indicates otherwise.

As used herein, various presence verbs "comprises," "includes" or "comprising," "including" when used in this specification, specify a presence of stated features, integers, steps, operations, elements, or components, but do not preclude the presence or addition of one or more other features, integers, steps, operations, elements, components, or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

As used herein, a term "or others," "combination", "combinatory," or "combinations thereof" refers to all permutations and combinations of listed items preceding that term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. Skilled artisans understand that typically there is no limit on number of items or terms in any combination, unless otherwise apparent from the context.

As used herein, unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized or overly formal sense unless expressly so defined herein.

As used herein, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" or "substantially" refers to a +/−10% variation from a nominal value/term. Such variation is always included in any given value/term provided herein, whether or not such variation is specifically referred thereto.

Figure 2:
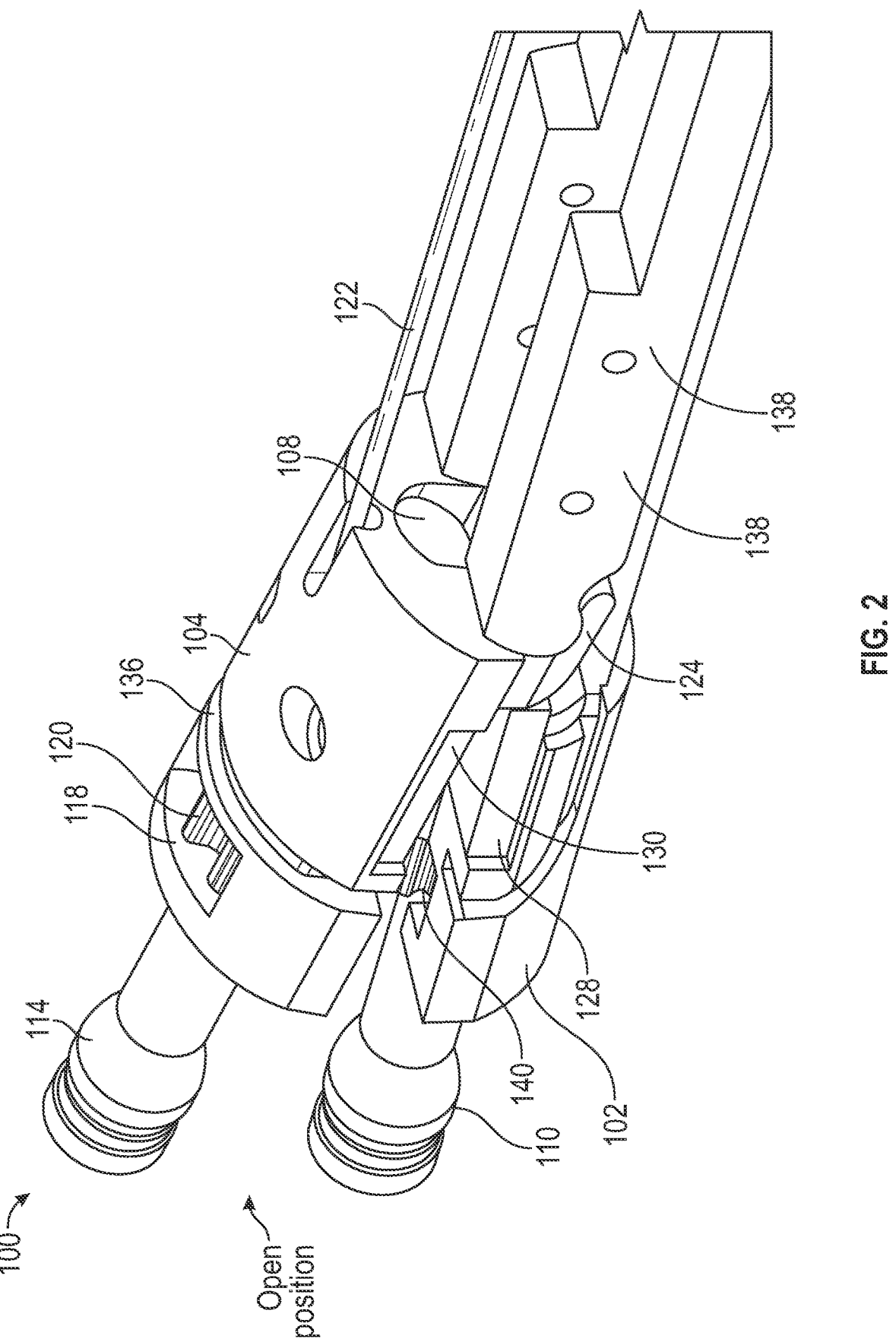
FIG. 2 shows a rear view of an embodiment of a needle driver in an open position according to this disclosure.
Figure 3:
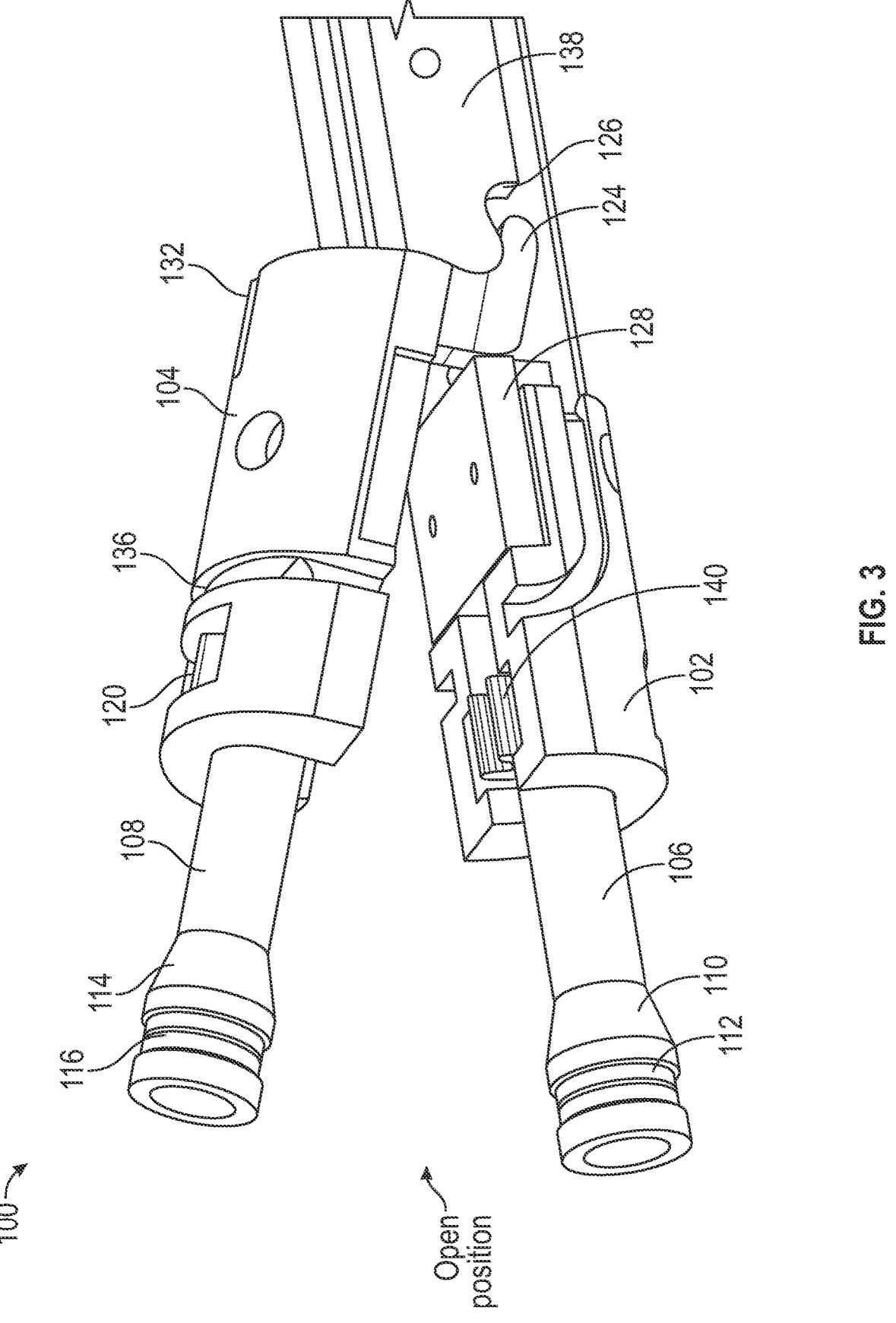
FIG. 3 shows a front view of an embodiment of a needle driver in an open position according to this disclosure.
Figure 4:
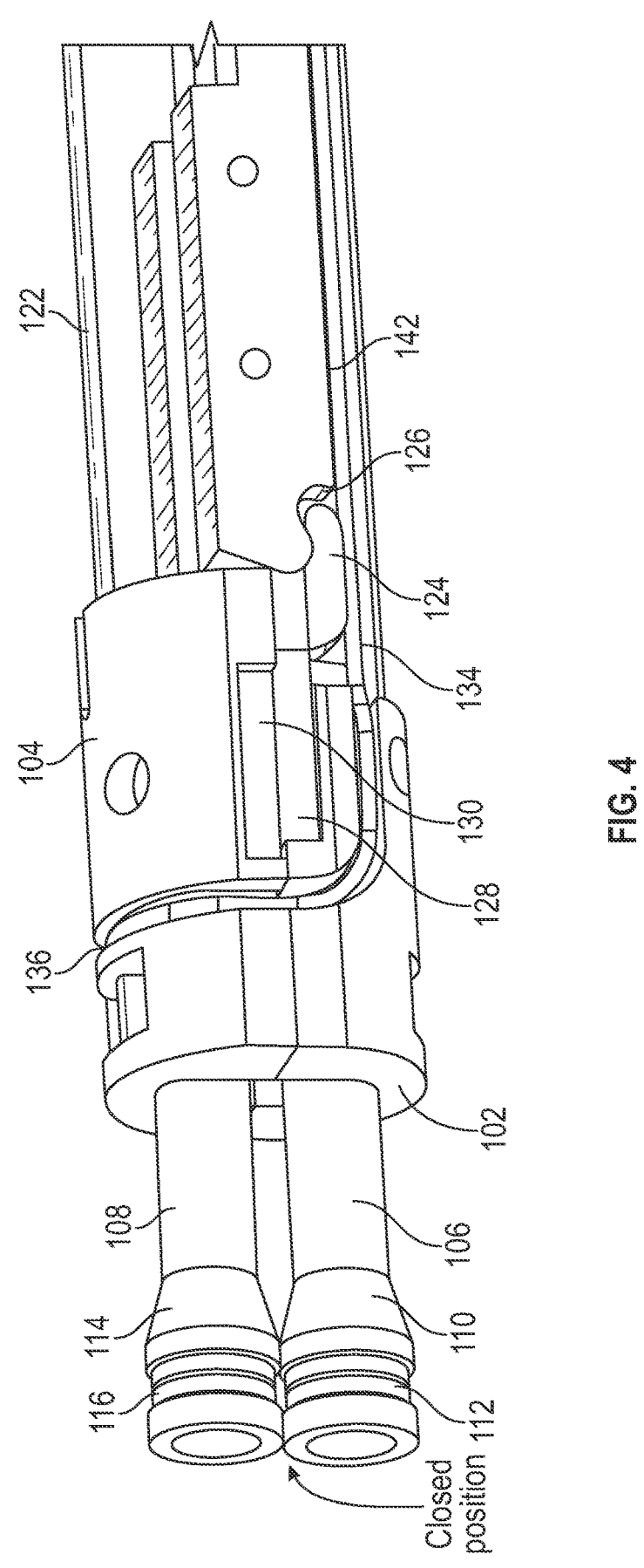
FIG. 4 shows a front view of an embodiment of a needle driver in a closed position according to this disclosure.
Figure 5:
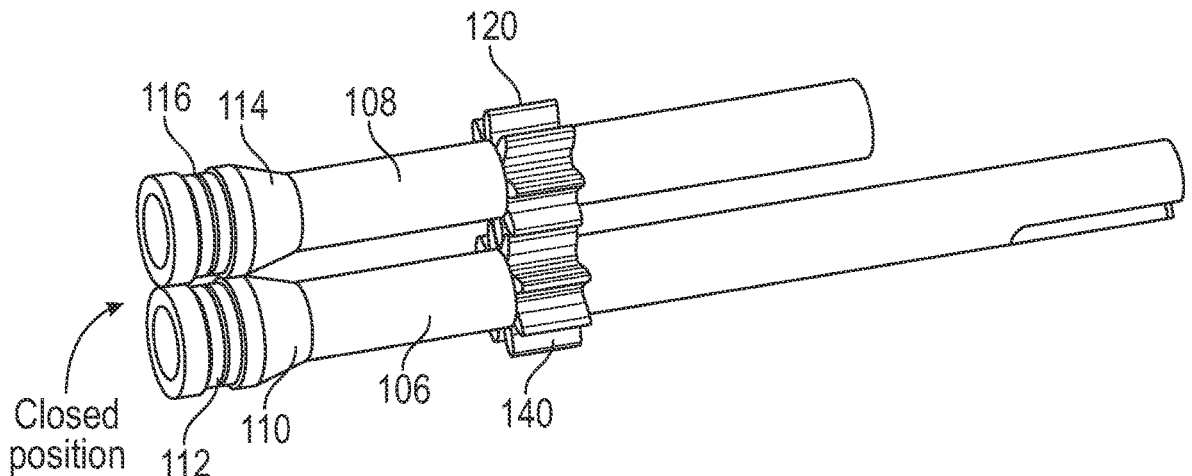
FIG. 5 shows a front view of an embodiment of a pair of shafts in a gear engagement according to this disclosure.
Figure 6:
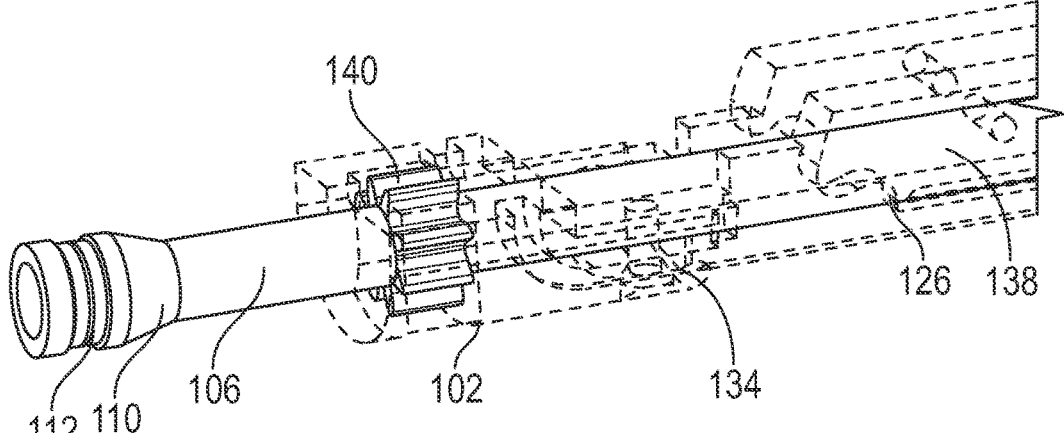
FIG. 6 shows a front view of an embodiment of a first jaw hosting a first shaft according to this disclosure.
Figure 7:
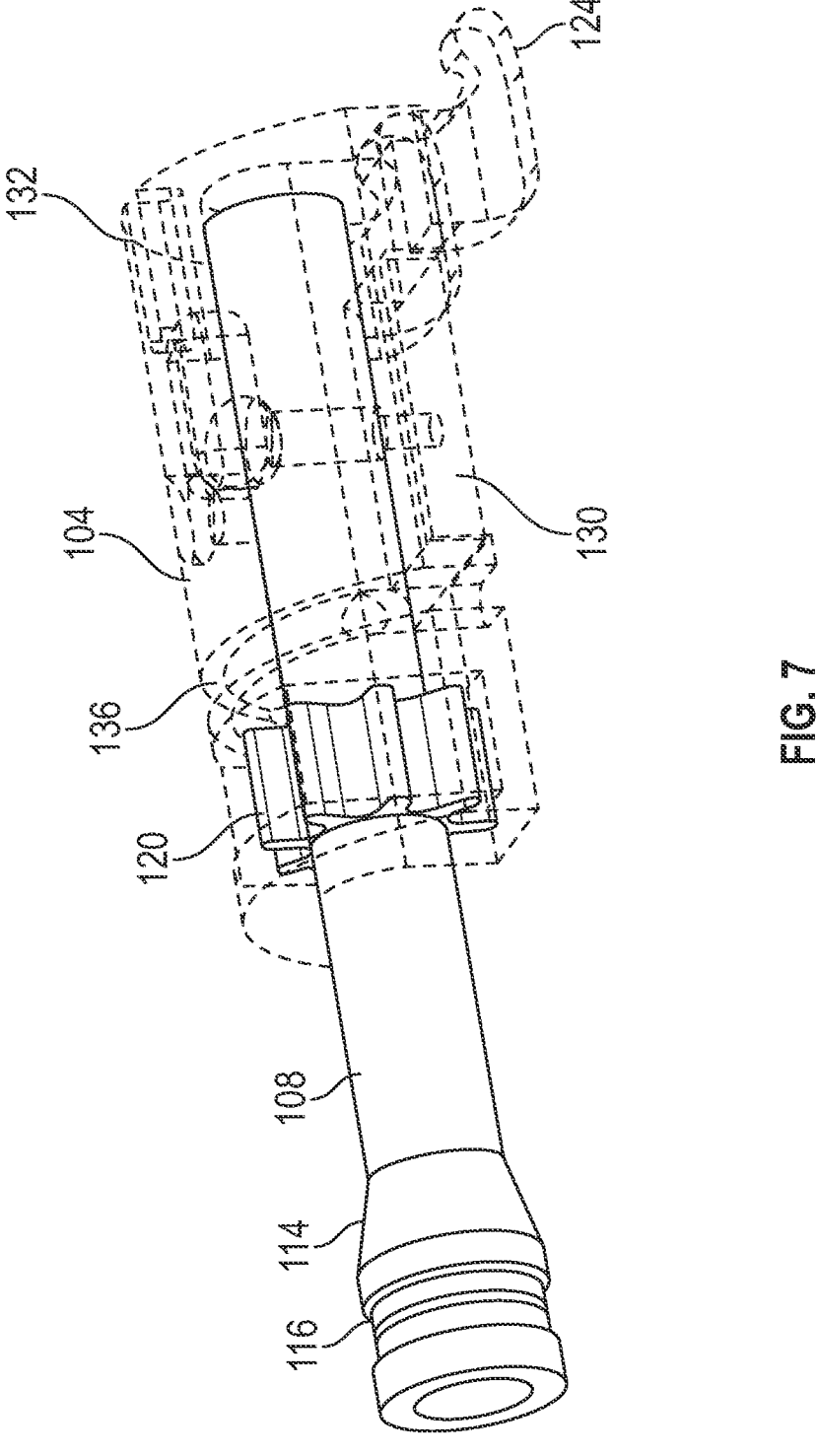
FIG. 7 shows a front view of an embodiment of a second jaw hosting a second shaft according to this disclosure.
Figure 8:
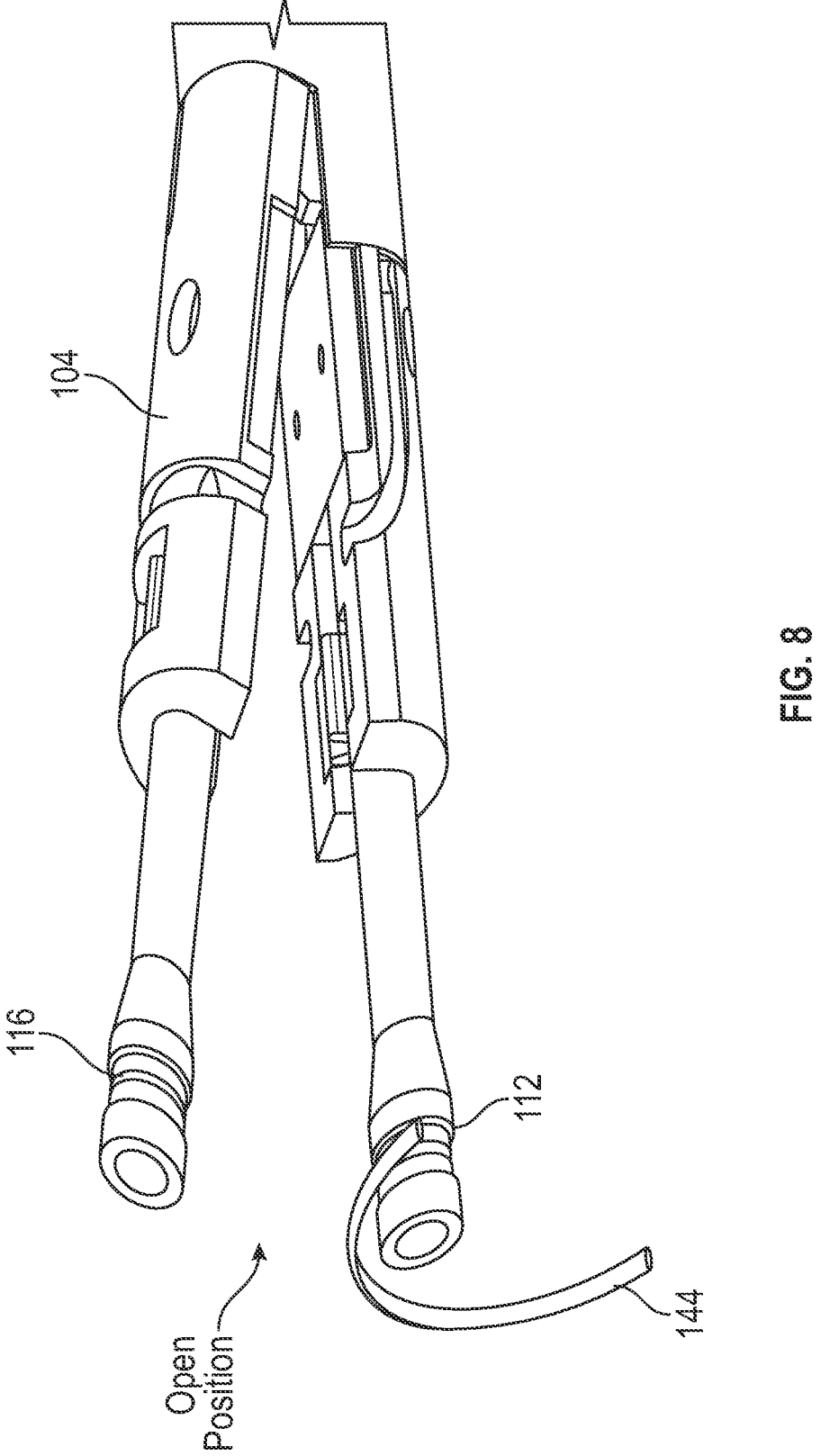
FIG. 8 shows a front view of an embodiment of a needle being inserted between a pair of rollers when the pair of rollers is in an open position according to this disclosure.
Figure 9:
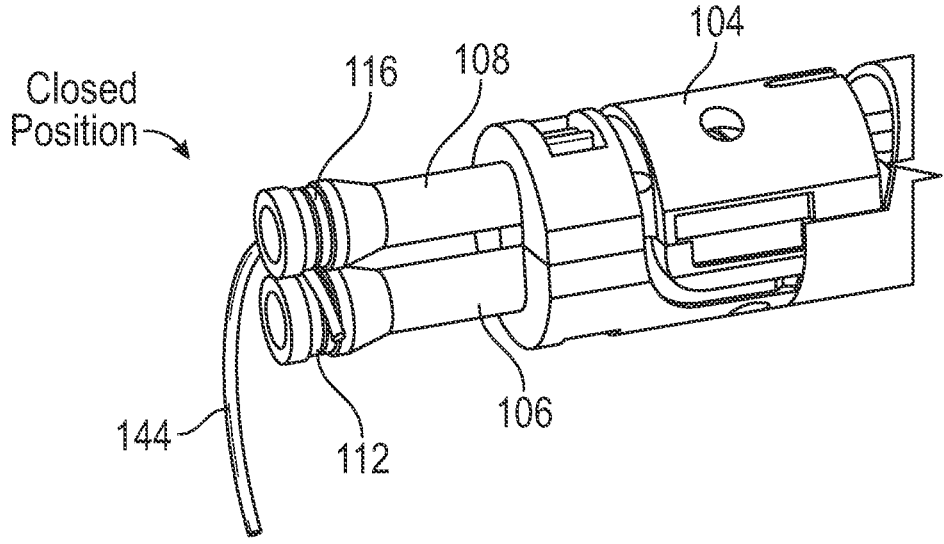
FIG. 9 shows a front view of an embodiment of a needle being engaged via a pair of rollers when the pair of rollers is in a closed position according to this disclosure.

FIG. 1 shows a rear view of an embodiment of a needle driver in a closed position according to this disclosure. FIG. 2 shows a rear view of an embodiment of a needle driver in an open position according to this disclosure. FIG. 3 shows a front view of an embodiment of a needle driver in an open position according to this disclosure. FIG. 4 shows a front view of an embodiment of a needle driver in a closed position according to this disclosure. FIG. 5 shows a front view of an embodiment of a pair of shafts in a gear engagement according to this disclosure. FIG. 6 shows a front view of an embodiment of a first jaw hosting a first shaft according to this disclosure. FIG. 7 shows a front view of an embodiment of a second jaw hosting a second shaft according to this disclosure. FIG. 8 shows a front view of an embodiment of a needle being inserted between a pair of rollers when the pair of rollers is in an open position according to this disclosure. FIG. 9 shows a front view of an embodiment of a needle being engaged via a pair of rollers when the pair of rollers is in a closed position according to this disclosure.

In particular, a needle driver 100 can be used for an open surgery, a minimally invasive surgery, a laparoscopic surgery, or an end effector robotic surgery. As such, the needle driver 100 can be used for manual surgery or automated surgery. Some examples of surgeries where the needle driver 100 can be employed include laparoscopic surgery, robotic surgery, video-assisted or unassisted thoracoscopic surgery, arthroscopic surgery, natural orifice surgery, endoscopic surgery, gynecologic surgery, cardiac surgery, colorectal surgery, pulmonary surgery, gastric bypass surgery, hysterectomy surgery, dental surgery, urological surgery, brain surgery, or bariatric surgery, or among many others in human (e.g., between newborn until 120 years old, male, female) or animal (e.g., mammal, birds, fish, land animals) applications.

The needle driver 100 includes a first jaw 102 hosting (e.g., holding, supporting, suspending) a first shaft 108 and a second jaw 104 hosting (e.g., holding, supporting, suspending) a second shaft 106. For example, the first jaw 102 can be embodied as a housing or a case. For example, the second jaw 102 can be embodied as a housing or a case. The second jaw 104 can be separate and distinct from the first jaw 102, but can be unitary therewith (e.g., monolithic, same material).

The first jaw 102 is shown as having a lateral cross-section that is hemispherical, but this shaping can vary (e.g., rectangular, square, triangular, oval). The second jaw 104 is shown as having a lateral cross-section that is hemispherical, but this shaping can vary (e.g., rectangular, square, triangular, oval). As shown in FIGS. 1 and 4, together, the first jaw 102 and the second jaw 104 define an oval lateral cross-section, although this shaping can vary (e.g., rectangular, square, triangular, circular). The first jaw 102 is longitudinally longer than the second jaw 104, although this can vary where the first jaw 102 can be longitudinally equivalent or longitudinally shorter than the second jaw 104. The first jaw 102 or the second jaw 104 include a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

As shown in FIGS. 1 and 4, the first shaft 106 extends parallel to the second shaft 108 between the first jaw 102 and the second jaw 104. Likewise, the first shaft 106 extends parallel to the second shaft 108 external to the first jaw 102 and to the second jaw 104. Similarly, the first shaft 106 and the second shaft 108 are positioned between the first jaw 102 and the second jaw 104.

The first shaft 106 and the second shaft 108 are rectilinear, but either or both can be non-rectilinear (e.g., arcuate, sinusoidal, pulse-shaped). The first shaft 106 or the second shaft 108 include a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The first shaft 106 can cantileveredly extend from the first jaw 102. The second shaft 108 can cantileveredly extend from the second jaw 104. The first shaft 106 can be parallel to the second shaft 108 external to the first jaw 102. The first shaft 106 can be parallel to the second shaft external to the second jaw 104. The first shaft 106 can be parallel to the second shaft 108 external to the first jaw 102 and to the second jaw 104. The first shaft 106 can be rotationally driven automatically (e.g., motor, engine, actuator, mechanical linkage, gear mechanism, pulley mechanism, hydraulic mechanism, pneumatic mechanism) or can be rotationally driven manually (e.g., user rotation).

The first jaw 102 has a first longitudinal axis and the second jaw 104 has a second longitudinal axis. As shown in FIGS. 1 and 4, the first longitudinal axis is parallel to the second longitudinal axis. As shown in FIGS. 2 and 3, the first longitudinal axis is not parallel (e.g., acute, obtuse, perpendicular) to the second longitudinal axis. Regardless, the first shaft 106 rotates about the first longitudinal axis. Likewise, the second shaft 108 rotates about the second longitudinal axis.

The first shaft 106 hosts a first roller 110 and a first set of teeth 140. For example, the first roller 110 can be embodied as a sleeve mounted onto the first shaft 106. The first roller 110 can be unitary (e.g., monolithic, same material) with the first shaft 106 or assembled with the first shaft 106 (e.g., adhering, fastening, mating, interlocking, magnetizing). For example, the first roller 110 can be mounted onto the first shaft 106 (e.g., end portion, not-end-portion, middle). For example, the first shaft 106 can include an end portion on which the first roller 110 is mounted, where the end portion is distal to the first jaw 102. For example, the first roller 110 can be a cap that is mountable onto the first shaft 106. The first roller 110 is diametrically larger than the first shaft 106, but this configuration can vary where the first roller 110 is diametrically equivalent or diametrically lesser than the first shaft 106. The first roller 110 can be external to the first jaw 102.

The first roller 110 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The first roller 110 includes a first groove portion 112, which has a plurality of grooves. The grooves define a plurality of peak/valley portions, male/female portions, or projection/depression portions, any of which can be perpendicular to the first roller 110 or non-perpendicular to the first roller 110 (e.g., acute, obtuse). For example, the grooves can be slanted, wavy, pulse-shaped, or others. For example, the grooves can be internally U-shaped, C-shaped, V-shaped, W-shaped, or others. The first roller 110 can avoid the first groove portion 112. In an embodiment, the first roller comprises a flat surface. In an embodiment, the first roller comprises a textured surface without grooves.

The first roller 110 has a conical end portion proximal to the first jaw 102 and a cylindrical portion that is circular and distal to the first jaw 102. However, note that this shaping can vary. For example, the conical end portion can be absent or the cylindrical portion can be rectangular, pentagonal, octagonal, triangular, oval, or others.

The first set of teeth 140 is or defines a gear, which can be a gear strip, a gear wheel, or others. For example, the gear can be a spur gear, a helical gear, or others. For example, the first shaft 106 can host a spur gear including the first set of teeth 140. However, note that other forms of gear are possible (e.g., bevel, linear, helical). The first set of teeth 140 can be unitary (e.g., monolithic, same material) with the first shaft 106 or assembled with the first shaft 106 (e.g., adhering, fastening, mating, interlocking, magnetizing). For example, the first set of teeth 140 can be mounted onto the first shaft 106 (e.g., end portion, not end portion, middle). For example, the first shaft 106 can include a not-end-portion or middle portion on which the first set of teeth 140 is mounted, where the not-end-portion is distal to the first roller 110. The first set of teeth 140 is housed within the first jaw 102, but can be housed outside the first jaw 102.

The first set of teeth 140 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The second shaft 108 hosts a second roller 114 and a second set of teeth 120. For example, the second roller 114 can be embodied as a sleeve mounted onto the second shaft 108. The second roller 114 can be unitary (e.g., monolithic, same material) with the second shaft 108 or assembled with the second shaft 108 (e.g., adhering, fastening, mating, interlocking, magnetizing). For example, the second roller 114 can be mounted onto the second shaft 108 (e.g., end portion, not-end-portion, middle). For example, the second shaft 108 can include an end portion on which the second roller 114 is mounted, where the end portion is distal to the second jaw 104. For example, the second roller 114 can be a cap that is mountable onto the second shaft 108. The second roller 114 is diametrically larger than the second shaft 108, but this configuration can vary where the second roller 114 is diametrically equivalent or diametrically lesser than the second shaft 108. The first shaft 106 can be longitudinally longer than the second shaft 108, but this configuration can vary (e.g., longitudinally equivalent, longitudinally shorter). The second roller 114 can be external to the second jaw 104. The second shaft 108 can be rotationally driven automatically (e.g., motor, engine, actuator, mechanical linkage, gear mechanism, pulley mechanism, hydraulic mechanism, pneumatic mechanism) or can be rotationally driven manually (e.g., user rotation).

The second roller 114 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The second roller 114 includes a second groove portion 116, which has a plurality of grooves. The grooves define a plurality of peak/valley portions, male/female portions, or projection/depression portions, any of which can be perpendicular to the second roller 114 or non-perpendicular to the second roller 114 (e.g., acute, obtuse). For example, the grooves can be slanted, wavy, pulse-shaped, or others. For example, the grooves can be internally U-shaped, C-shaped, V-shaped, W-shaped, or others. The second roller 114 can avoid the second groove portion 116. In an embodiment, the second roller comprises a flat surface. In an embodiment, the second roller comprises a textured surface without grooves.

The second roller 114 has a conical end portion proximal to the second jaw 104 and a cylindrical portion that is circular and distal to the second jaw 104. However, note that this shaping can vary. For example, the conical end portion can be absent or the cylindrical portion can be rectangular, pentagonal, octagonal, triangular, oval, or others. Further, the first roller 110 and the second roller 114 can be identical or non-identical to each other in terms of material, properties, or dimensions (e.g., length, width, thickness, diameter, radius). For example, although the first roller 110 and the second roller 114 are identical in length (or other dimensions), the first roller 110 and the second roller 114 can be non-identical in length (or other dimensions).

The second set of teeth 120 is or defines a gear, which can be a gear strip, a gear wheel, or others. For example, the gear can be a spur gear, a helical gear, or others. The second shaft 108 can host a spur gear including the second set of teeth 120. However, note that other forms of gear are possible (e.g., bevel, linear, helical). The second set of teeth 120 can be unitary (e.g., monolithic, same material) with the second shaft 108 or assembled with the second shaft 108 (e.g., adhering, fastening, mating, interlocking, magnetizing). For example, the second set of teeth 120 can be mounted onto the second shaft 108 (e.g., end portion, not end portion, middle). For example, the second shaft 108 can include a not-end-portion or middle portion on which the second set of teeth 120 is mounted, where the not-end-portion is distal to the second roller 114. The second set of teeth 120 is housed within the second jaw 104, but can be housed outside the second jaw 104. For example, the first roller 106 can host a first spur gear including the first set of teeth 140 and the second roller 108 can host a second spur gear including the second set of teeth 120, where the first spur gear engages the second spur gear such that the first spur gear drives the second spur gear.

The second jaw 104 defines an opening 118. The opening 118 is arcuate and rectangular, but this shaping can vary (e.g., rectilinear, square, dimpled, circle, triangular). The opening 118 provides a physical access or a visible access to the second set of teeth 120, such as for maintenance, if needed. The second jaw 104 can avoid defining the opening 118.

The second set of teeth 120 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

As shown in FIGS. 1 and 4, the first groove portion 112 faces the second groove portion 116 and the first groove portion 112 can contact the second groove portion 116. Likewise, the first set of teeth 140 and the second set of teeth 120 are positioned between the first jaw 102 and the second jaw 104. Similarly, the first set of teeth 140 can mesh with the second set of teeth 120. However, note that variations are possible. For example, the first groove portion 112 can be longitudinally offset relative to the second groove portion 116 or vice versa. Likewise, the first set of teeth 140 or the second set of teeth 120 can be positioned outside the first jaw 102 or the second jaw 104.

The second jaw 104 defines a channel 132. The channel 132 is internally open (e.g., U-shaped, C-shaped, V-shaped, W-shaped), but can be internally closed (e.g., O-shaped, D-shaped). The second jaw 104 can avoid defining the channel 132.

The second jaw 104 is coupled to a first end portion of a line 122 as the line 122 extends through the channel 132.

The line 122 can be embodied in various ways (e.g., tether, string, cable, chain, strap, rope, braid, bar, shaft, planar member). The line 122 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The first end of the line 122 can be coupled to the second jaw 104 in various ways (e.g., knot, adhering, fastening, lassoed). The line 122 has a second end portion coupled to a control interface. The second end of the line 122 can be coupled to the control interface in various ways (e.g., knot, adhering, fastening, lassoed). However, note that this configuration can vary, such as where the line is U-shaped or C-shaped and the first end of the line 122 and the second end of the line 122 are coupled to the control interface and a non-end portion of the line 122 (e.g., middle portion) is coupled (e.g., looped, hooked) to the second jaw 104.

The control interface can be a manual interface or an automated interface. For example, the manual interface can include a user input device (e.g., trigger, button, switch, dial, lever). For example, the automated interface can include a mover (e.g., motor, engine, actuator, mechanical linkage, gear mechanism, pulley mechanism, hydraulic mechanism, pneumatic mechanism). For example, the automated interface can be included in a robot (e.g., articulating arm, single or multi-joint end effector). For example, the needle driver 100 can include a distal portion hosting the first jaw 102 and the second jaw 104 and a proximal portion hosting the control interface. For example, the end effector can host (e.g., support, suspend, fasten, mate, interlock) the first jaw 102 or the second jaw 104. For example, the first jaw 102 and the second jaw 104 can be housed in a housing (e.g., tube, case, encasement, arm). For example, the housing includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The second jaw 104 includes a male portion 124 (e.g., tail) extending therefrom. The male portion 124 can be unitary (e.g., monolithic, same material) with the second jaw 104 or assembled with the second jaw 104 (e.g., adhering, fastening, mating, interlocking, magnetizing, mounting). For example, the male portion 124 can be distal to the second set of teeth 120. The male portion 124 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The first jaw 104 defines a female portion 126 extending thereinto. The female portion 126 is structured to mate with the male portion 124 or vice versa. As such, the male portion 124 is inserted into the female portion 126 such that a coupling relationship is established.

The coupling relationship can enable the second jaw 104 to move relative to the first jaw 102 between an open position, as shown in FIGS. 2 and 3, and a closed position, as shown in FIGS. 1 and 4. For example, the second jaw 104 can move relative to the first jaw 102 via pivoting, rotation, sliding, or others, or any combination of the foregoing. For example, the second jaw 104 can move between the closed position and the open position relative to the first jaw 102 inclusively about or less than 180, 175, 170, 165, 160, 155, 150, 145, 140, 135, 130, 125, 120, 115, 110, 105, 100, 95, 90, 85, 80, 75, 70, 65, 60, 55, 50, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 degrees. For example, the second jaw 104 can form an angle relative to the first jaw 102, where the angle can be acute, perpendicular, or obtuse. For example, the first shaft 106 can be not parallel to the second shaft 108 in the open position. For example, the second jaw 104 can be biased open (e.g., spring, elastic member) or biased closed (e.g., spring, elastic member) relative to the first jaw 102. For example, the second jaw 104 can be default position open or default position closed relative to the first jaw 102. In other embodiments, the second jaw 104 can move between the closed position and the open position relative to the first jaw 102 inclusively about or less than 360, 345, 330, 315, 300, 285, 270, 255, 240, 225, 210, 195, 180, 165, 150, 135, 120, 105, 90, 80, 70, 60, 50, 45, 40, 35, 30, 25, 20, 15, 10, and 5 degrees, or less than 5 degrees.

The closed position can be a terminal position (e.g., last, extreme, lower bound) or the open position is a terminal position (e.g., last, extreme, upper bound). For example, the second jaw 104 has a range of motion spanning between the closed position and the open position. However, this configuration can vary where the closed position is not a terminal position (e.g., within range of positions, between terminal positions) or the open position is not a terminal position (e.g., within range of positions, between terminal positions).

The first set of teeth 140 meshes with the second set of teeth 120 when the second jaw 102 is in the closed position such that (a) the first set of teeth 140 can drive (e.g., rotationally) the second set of teeth 120 and (b) the first roller 110 and the second roller 114 can drive a needle (e.g., rectilinear, non-rectilinear, arcuate, helical, spiral) therebetween when the first set of teeth 140 drives (e.g., rotationally) the second set of teeth 120. The first set of teeth 140 can avoid meshing with the second set of teeth 120 when the second jaw 104 is in the open position. However, note that in some open positions at least some meshing between the first set of teeth 140 can avoid meshing with the second set of teeth 120 can be possible.

In the open position or in the closed position, the first set of teeth 140 can be exposed to the second jaw 102 when the second jaw 102 is in the open position. Likewise, the first set of teeth 140 can be exposed to the second set of teeth 120 when the second jaw 102 is in the open position. Similarly, the second set of teeth 120 can be exposed to the first jaw 102 when the second jaw 104 is in the open position. Also, the second set of teeth 120 can be exposed to the first set of teeth 140 when the second jaw 104 is in the open position. Additionally, the first set of teeth 140 and the second set of teeth 120 can be positioned between the first jaw 102 and the second jaw 104.

In the coupling relationship between the first jaw 102 and the second jaw 104, the second jaw 104 can be hingedly coupled to the first jaw 102 such that the second jaw 104 can move relative to the first jaw 102 between the open position and the closed position. For example, the first jaw 102 or the second jaw 104 can host a hinge (e.g., spring, barrel, pivot, butt, mortise, case, continuous, piano, concealed, butterfly, flag, strap, biased). For example, the first jaw 102 or the second jaw 104 can be attached, fastened, mated, interlocked, adhered, or magnetized to the hinge. The second jaw 104 can be hingedly coupled to the first jaw 102 without using a pin (e.g., rectilinear pin, arcuate pin, sinusoidal pin)

about which the second jaw 104 moves relative to the first jaw 102 between the open position and the closed position. However, note that the second jaw 104 can be hingedly coupled to the first jaw 102 via a pin (e.g., rectilinear pin, arcuate pin, sinusoidal pin) about which the second jaw 104 moves relative to the first jaw 102 between the open position and the closed position, where the pin laterally traverses the first jaw 102 or the second jaw 104.

In the coupling relationship between the first jaw 102 and the second jaw 104, the second jaw 104 can be pivotally coupled to the first jaw 102 such that the second jaw 104 moves relative to the first jaw 102 between the open position and the closed position. The second jaw 104 can be pivotally coupled to the first jaw 102 without using a pin about which the second jaw 104 moves relative to the first jaw 102 between the open position and the closed position. However, note that the second jaw 104 can be pivotally coupled to the first jaw 102 via a pin (e.g., rectilinear pin, arcuate pin, sinusoidal pin) about which the second jaw 104 moves relative to the first jaw 102 between the open position and the closed position, where the pin laterally traverses the first jaw 102 or the second jaw 104.

As shown in FIGS. 1-4, the first jaw 102 includes the female portion 126 and the first set of teeth 140 is positioned between the first roller 110 and the female portion 126. Correspondingly, the second jaw 104 includes the male portion 124 and the second set of teeth 120 is positioned between the second roller 114 and the male portion 124. Resultantly, the female portion 126 and the male portion 114 pivotably mate such that the second jaw 104 moves relative to the first jaw 102 between the open position and the closed position. The second jaw 104 can be pivotably mated to the first jaw 102 without using a pin (e.g., rectilinear pin, arcuate pin, sinusoidal pin) about which the second jaw 104 moves relative to the first jaw 102 between the open position and the closed position. However, the second jaw 104 can be pivotably mated to the first jaw 102 via a pin (e.g., rectilinear pin, arcuate pin, sinusoidal pin) about which the second jaw 104 moves relative to the first jaw 102 between the open position and the closed position, where the pin laterally traverses the first jaw 102 or the second jaw 104.

The second jaw 104 can move relative to the first jaw from the closed position to the open position based on the line 122 being pulled in a direction away from the first jaw 102, the second jaw 104, the first set of teeth 140, the second set of teeth 140, the first roller 110, or the second roller 114. For example, the direction can be longitudinal to the first jaw 102, but can include a vertical component or a lateral component. Note that another configuration is possible where the line 122 can be moved from the open position to the closed position based on the line 122 being pushed in a direction toward the first jaw 102, the second jaw 104, the first set of teeth 140, the second set of teeth 140, the first roller 110, or the second roller 114. Note that in such configuration the line 122 can be sufficiently rigid to enable such force application.

As shown in FIGS. 1-4, the first jaw 102 and the second jaw 104 are self-aligning when moving from the open position to the closed position or in the closed position. However, this can vary, such as when the first jaw 102 and the second jaw 104 are not self-aligning when moving from the open position to the closed position or in the closed position. For example, the first jaw 102 and the second jaw 104 can be misaligned or offset relative to each other in the closed position.

As shown in FIGS. 2 and 3, the second shaft 108 is rotationally unconstrained in the open position. For example, the second shaft 108 can rotate freely, whether clockwise or counterclockwise, in the open position (e.g., continual rotation, several full rotations, less than one full rotation, inclusively about 720, 360, 270, 180, 120, 90, 75, 60, 50, 45, 33, 30, 20, 15, 10, or 5 degrees or more or less). However, this configuration can vary and the second shaft 108 can be rotationally constrained in the open position (e.g., locked).

The first jaw 102 hosts a retaining block 128. For example, the retaining block 128 can be fastened, adhered, mated, interlocked, mounted, or magnetized to the first jaw 102. The retaining block 128 is positioned between the first shaft 106 and the second shaft 108, which can occur when the second jaw 104 is in the closed position or in the open position. The retaining block 128 is square shaped, but this shaping can vary (e.g., circular, oval, triangular, pentagonal, octagonal, rectangular). The retaining block 128 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The second jaw 104 hosts a retaining block 130. For example, the retaining block 130 can be fastened, adhered, mated, interlocked, mounted, or magnetized to the second jaw 104. The retaining block 130 is positioned between the first shaft 106 and the second shaft 108, which can occur when the second jaw 104 is in the closed position or in the open position. The retaining block 130 is square shaped, but this shaping can vary (e.g., circular, oval, triangular, pentagonal, octagonal, rectangular). The retaining block 130 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others. Although the retaining block 128 and the retaining block 130 are identical in shape, size, material, and orientation, the retaining block 128 and the retaining block 130 can be non-identical in shape, size, material, and orientation.

As shown in FIGS. 1 and 4, in the closed position, the retaining block 128 and the retaining block 130 face each other or contact each other. In some configurations, the retaining block 128 and the retaining block 130 are magnetically attracted to each other or magnetically repulsed from each other. As shown in FIGS. 2 and 3, in the open position, the retaining block 128 and the retaining block 130 face each other, but this can vary with angling of the second jaw 104 relative to the first jaw 102. For example, when the second jaw 104 is in the open position and angled more than 90 degrees relative to the first jaw 104, then the retaining block 128 and the retaining block 130 can avoid facing each other, yet still be exposed to each other. However, when the second jaw 104 is in the open position and angled less than 90 degrees relative to the first jaw 104, then the retaining block 128 and the retaining block 130 can face and be exposed to each other.

The first jaw 102 can host the retaining block 128 between the first shaft 106 and the second shaft 108. The second jaw 104 can host the retaining block 130 between the first shaft 106 and the second shaft 108. The retaining block 128 can contact the retaining block 130 when the second jaw 104 is in the closed position.

The first jaw 102 defines a plurality of lateral channels 134 that longitudinally extend along the first jaw 102 parallel to the first shaft 106. The lateral channels 134 oppose each other on the first jaw 102, but can avoid opposing each other as well (e.g., offset relative to each other). The lateral channels 134 are rectilinear, but can be non-rectilinear (e.g., arcuate, sinusoidal). For example, the lateral channels 134 can define a plurality of ledges or shelves on the first jaw 102, whether rectilinear or non-rectilinear. The lateral channels 134 can be open or be internally U-shaped, C-shaped, V-shaped, W-shaped, or others. The lateral channels 134 can be closed or be internally D-shaped, O-shaped, or others. Note that the lateral channels 134 can avoid longitudinal extension parallel to the first shaft 106 (e.g., merging toward each other, diverging from each other). Further, note that the first jaw 102 can avoid the lateral channels 134.

The second jaw 104 defines a channel 136 that longitudinally extends lateral to the second jaw 104, while being non-parallel to the second shaft 108 (e.g., perpendicular, acute, obtuse). The channel 136 is rectilinear, but can be non-rectilinear (e.g., arcuate, sinusoidal). The channel 136 is longitudinally arcuate, but can be longitudinally rectilinear when the second jaw 104 is configured accordingly. The channel 136 can be open or be internally U-shaped, C-shaped, V-shaped, W-shaped, or others. The channel 136 can be closed or be internally D-shaped, O-shaped, or others. Note that the second jaw 104 can avoid the channel 136.

The first jaw 102 hosts a plurality of lateral walls 138 that longitudinally extend along the first jaw 102 parallel to the first shaft 106. The lateral walls 138 oppose each other on the first jaw 102, but can avoid opposing each other as well (e.g., offset relative to each other). The lateral walls 138 are rectilinear, but can be non-rectilinear (e.g., arcuate, sinusoidal). Each of the lateral walls 138 defines the female portion 126 corresponding thereto. As such, the lateral walls 138 allow the second jaw 104 to move relative to the first jaw 102 via the walls 138 functioning as a support structure to the second jaw 104. Note that the lateral walls 138 can avoid longitudinal extension parallel to the first shaft 106 (e.g., merging toward each other, diverging from each other).

As shown in FIG. 4, the first jaw hosts a line 142 extending within the lateral channels 134 within the channel 136 over the second jaw 104. The line 142 extends in three directions: a first direction (towards the first jaw 102, the second jaw 104, the first set of teeth 140, the second set of teeth 140, the first roller 110, or the second roller 114), a second direction (laterally traversing the second jaw 104 nonparallel to the first shaft 106 or the second shaft 108), and a third direction (away from the first jaw 102, the second jaw 104, the first set of teeth 140, the second set of teeth 140, the first roller 110, or the second roller 114). When observed from a lateral side profile view, the line 142 extends in an L-shape when the line 142 extends from one of the lateral channels 134 within the channel 136 over the second jaw 104. When observed from a top view, the line 142 extends in a U-shape when the line 142 extends from one of the lateral channels 134 within the channel 136 over the second jaw 104. Note that these shapes of extension can vary. For example, the line 142 can extend in a V-shape or a J-shape or an S-shape or a W-shape from the lateral side profile view. Likewise, the line 142 can extend in a C-shape or a V-shape or an S-shape from the top view.

The line 142 can avoid going over the second jaw 104 or spanning between the lateral channels 134. For example, the line 142 can stop somewhere (e.g., middle portion, non-middle portion) on the second jaw 104 (e.g., J-shape extension, L-shape extension). For example, the line 142 can be at least two different lines 142, which can be unconnected to each other in proximity of the second jaw 104 yet extending within the lateral channels 134 and each still being separately coupled to the second jaw 104 (e.g., knot, adhering, fastening, lassoed) in a manner, whether identical or non-identical to each other.

The line 142 can be embodied in various ways (e.g., tether, string, wire, cable, chain, strap, rope, braid, bar, shaft, planar member). The line 142 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The line 142 has a plurality of end portions coupled to a control interface (same one as described above or different one). These end portions can be coupled to the control interface in various ways (e.g., knot, adhering, fastening, lassoed). However, note that this configuration can vary, such as when there are different control interfaces.

The control interface can be a manual interface or an automated interface. For example, the manual interface can include a user input device (e.g., trigger, button, switch, dial, lever). For example, the automated interface can include a mover (e.g., motor, engine, actuator, mechanical linkage, gear mechanism, pulley mechanism, hydraulic mechanism, pneumatic mechanism). For example, the automated interface can be included in a robot (e.g., articulating arm, single or multi-joint end effector). For example, the needle driver 100 can include a distal portion hosting the first jaw 102 and the second jaw 104 and a proximal portion hosting the control interface.

As shown in FIGS. 2-4, the line 142 extends along the first jaw 102 (e.g., within lateral channels 134) and over the second jaw 104 (e.g., within channel 136) when the second jaw 104 is in the closed position or the open position. Therefore, the first set of teeth 140 can extend between the first roller 110 and the line 142, which can be in the closed position or in the open position. The second set of teeth 120 can extend between the second roller 114 and the line 142, which can be in the closed position or in the open position. Since the first jaw 102 can host the lateral channel 134, then the line 142 can extend along the lateral channel 134 before extending over the second jaw 104. The line 142 can extend along the first jaw 102 and over the second jaw 104 when the second jaw 104 is in the closed position or in the open position. The line 142 can extend along the first jaw 102 toward the first set of teeth 140 and away from the first set of teeth 140. Since the first jaw 102 can host the lateral channel 134, then the line 142 can extend along the lateral channel 134 after extending over the second jaw 104, which can be away from the first jaw 102, the second jaw 104, the first set of teeth 140, the second set of teeth 140, the first roller 110, or the second roller 114. Since the lateral channels 134 can oppose each other, then the line 142 can extend along the lateral channels 134, where at least two portions of the line 142 can oppose each other. Since the lateral channels 134 can oppose each other, the line 142 can also span between the lateral channels 134.

The line 142 can move the second jaw 104 between the open position and the closed position. The line 142, when pulled from the end portions thereof, can cause the second jaw 104 to move from the open position to the closed position. The second jaw 104 can move from the open position to the closed position based on a tension applied to the line 142, where the tension is in a direction away from the second set of teeth 120. The second jaw 104 can move from the open position to the closed position based on a tension applied to the line 142, where the tension is in a direction away from the second roller 114. The second jaw 104 can move from the open position to the closed position based on a tension applied to the line 142, where the tension is in a direction away from the second jaw 104. The second jaw 104 can move from the open position to the closed position based on the line 142 being pulled in a direction away from the second set of teeth 120. The second jaw 104 can move from the open position to the closed position based on the line 142 being pulled in a direction away from the second roller 114. The second jaw 104 can move from the open position to the closed position based on the line 142 being pulled in a direction away from the second jaw 104.

Note that various combinatorics of above are possible. For example, the second jaw 104 can move from the open position to the closed position based on the line 142 being pulled in a direction away from at least two of the second set of teeth 120, the second roller 114, or the second jaw 104. For example, since the first jaw 102 hosts the lateral channels 134 that oppose each other, then the line 142 can extend along the lateral channels 134 and the second jaw 104 can move from the open position to the closed position based on the line 142 being pulled in a plurality of directions away from at least one of the second set of teeth 120, the second roller 114, or the second jaw 104. The directions can be identical or non-identical to each other. The directions can be parallel or non-parallel to each other. The directions can be toward a same area or point.

As shown in FIGS. 1 and 4, the first roller 110 and the second roller 114 can clamp or grab an object therebetween when the second jaw is in the closed position. The object can be animate or inanimate. For example, the object when animate can include a tissue, an organ, a body part, whether of human or animal, or others. For example, the tissue can be a muscle tissue, a bone tissue, a nerve tissue, an organ tissue, or others. For example, the object when inanimate can include a medical device, a prosthesis, an implantable, a machine, a surgical instrument, or others. The closed position can be a clamping position.

As shown in FIG. 8, the second jaw 104 is in the open position and a needle 144 is positioned on the first groove portion 112. For example, the needle 144 can be positioned within the first groove portion 112. The needle 144 is arcuate, but can be shaped non-arcuate (e.g., rectilinear, non-rectilinear, sinusoidal, helical). The needle 144 can be one of a group of needles, where the needles can vary from each other based on at least one of a size, a cross-sectional-shape, a lateral profile, a material, a longitudinal shape, or a lateral diameter.

The needle 144 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

As shown in FIG. 9, the second jaw 104 is in the closed position and the needle 144 is positioned between the first groove portion 112 and the second groove portion 116. For example, the needle 144 can be interposed or sandwiched between the first groove portion 112 and the second groove portion 116. As such, the needle 144 can be rotationally driven between the first groove portion 112 and the second groove portion 116 based on the first shaft 106 being driven (or the second shaft 108 being driven) when the second jaw 104 is in the closed position.

As shown in FIG. 9, the needle 144 can be driven rotationally about an axis parallel to the first shaft 106 when the needle 144 is positioned between the first roller 106 and the second roller 108. Likewise, the needle 144 can be driven rotationally about an axis parallel to the second shaft 108 when the needle 144 is positioned between the first roller 106 and the second roller 108. Similarly, the needle 144 can be driven rotationally about an axis parallel to the first shaft 106 and to the second shaft 108 when the needle 144 is positioned between the first roller 106 and the second roller 108. However, note that the needle 144 driven rotationally about an axis non-parallel (e.g., perpendicular, obtuse, acute) to the first shaft 106 when the needle 144 is positioned between the first roller 106 and the second roller 108. Likewise, the needle 144 can be driven rotationally about an axis non-parallel (e.g., perpendicular, obtuse, acute) to the second shaft 108 when the needle 144 is positioned between the first roller 106 and the second roller 108. Similarly, the needle 144 driven rotationally about an axis non-parallel (e.g., perpendicular, acute, obtuse) to the first shaft 106 and to the second shaft 108 when the needle 144 is positioned between the first roller 106 and the second roller 108. Also, the needle 144 can be driven rotationally about an axis perpendicular to the first shaft 106 or the second shaft 108 when the needle 144 is positioned between the first roller 106 and the second roller 108.

The first shaft 106 can rotate between about 0 degrees and about 360 degrees or greater, which can include a plurality of full revolutions (e.g., about 720 degrees, about 1080 degrees, or more). For example, the first shaft 106 or the second shaft 108 can rotate at least about 180 degrees, about 270 degrees, or about 360 degrees, when the needle 144 is positioned between the first roller 106 and the second roller 108.

Figure 10:
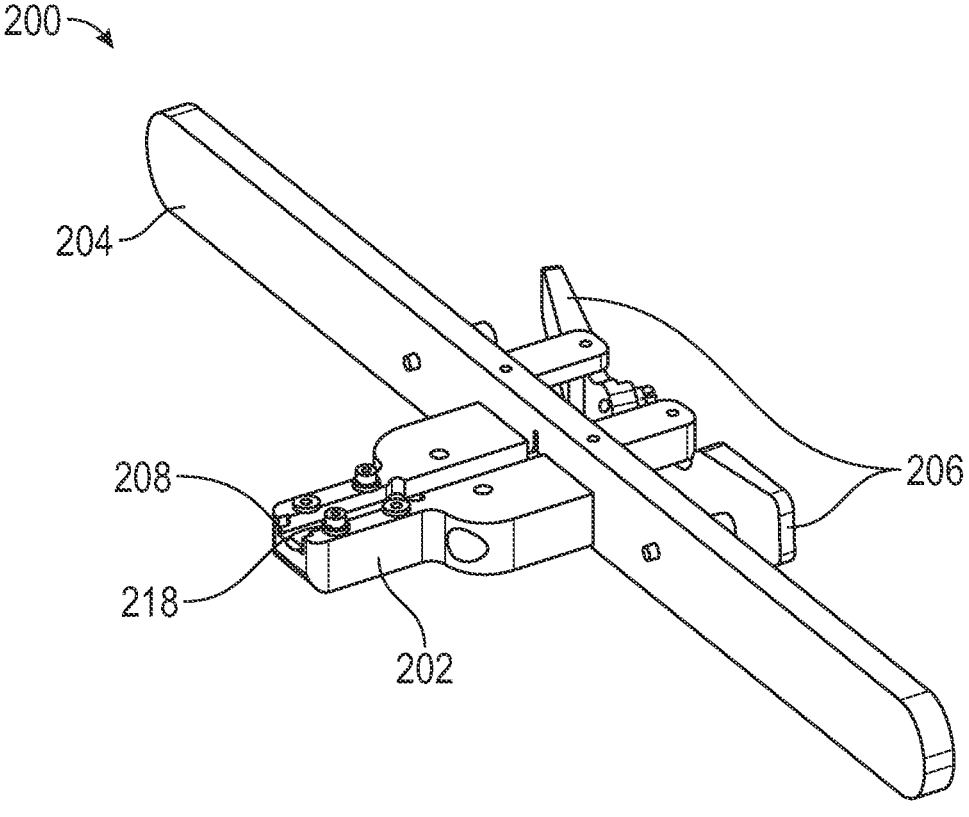
FIG. 10 shows a front view of an embodiment of a testing device for a needle driver according to this disclosure.
Figure 11:
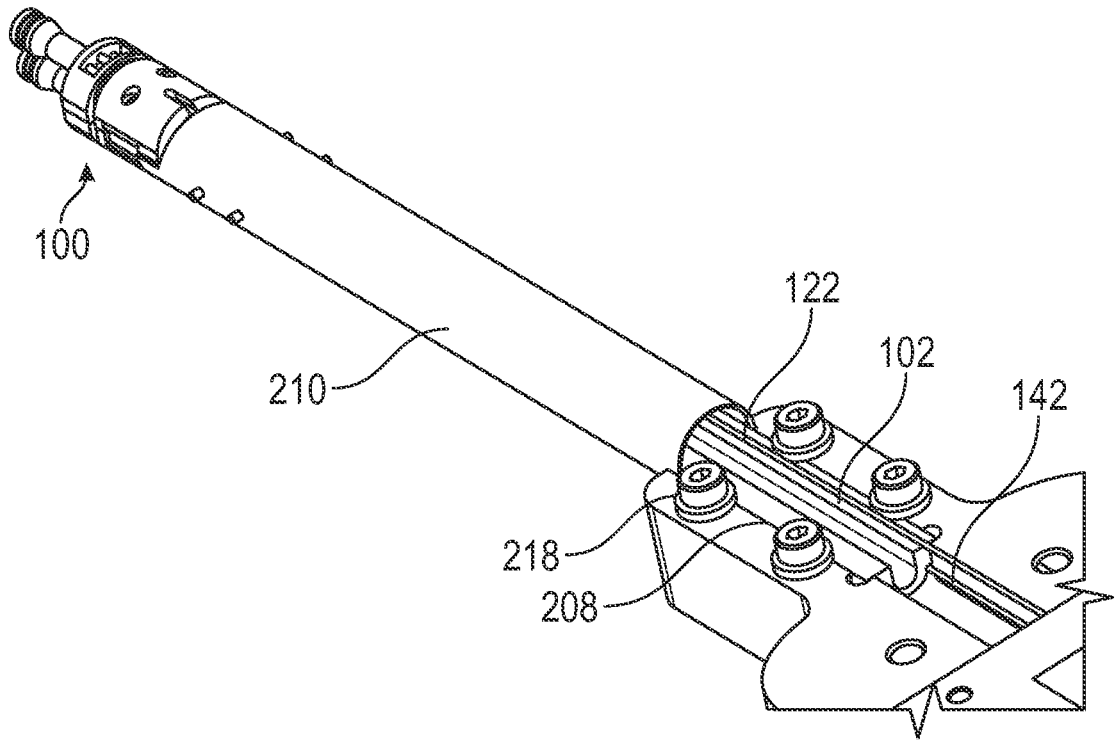
FIG. 11 shows a rear view of an embodiment of a testing device hosting a needle driver according to this disclosure.
Figure 12:
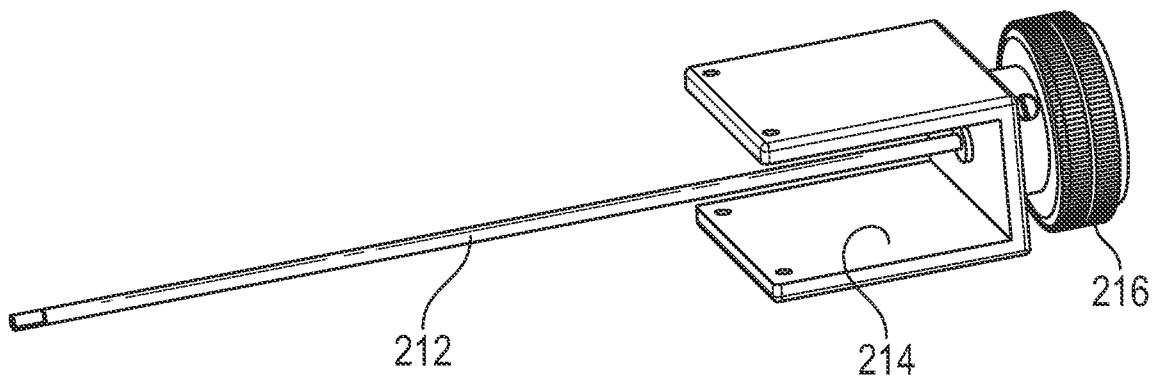
FIG. 12 shows a front view of an embodiment of a rotary mechanism for a needle driver according to this disclosure.
Figure 13:
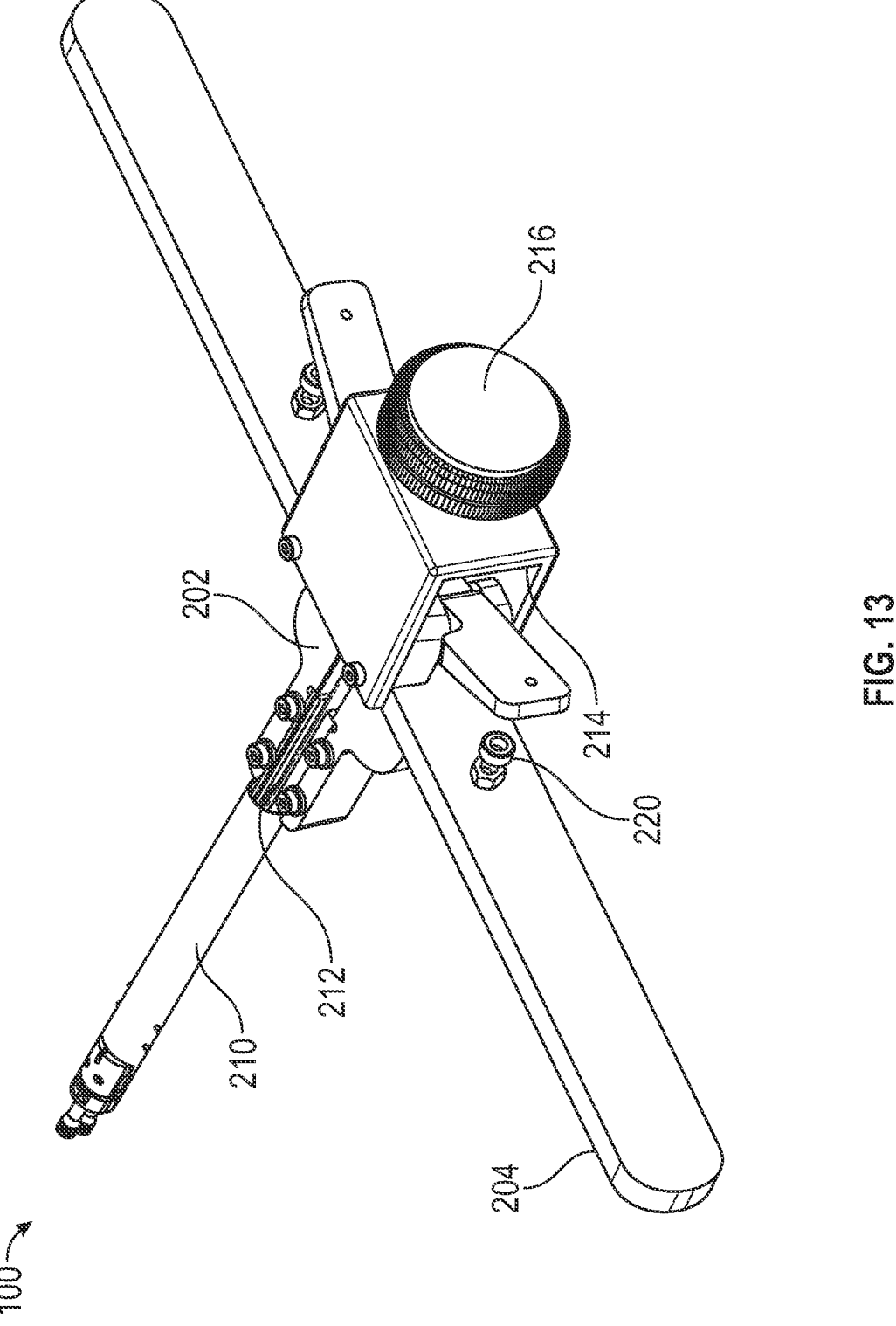
FIG. 13 shows a rear view of an embodiment of a testing device with a rotary mechanism hosting a needle driver according to this disclosure.

FIG. 10 shows a front view of an embodiment of a testing device for a needle driver according to this disclosure. FIG. 11 shows a rear view of an embodiment of a testing device hosting a needle driver according to this disclosure. FIG. 12 shows a front view of an embodiment of a rotary mechanism for a needle driver according to this disclosure. FIG. 13 shows a rear view of an embodiment of a testing device with a rotary mechanism hosting a needle driver according to this disclosure. In particular, a testing device 200 can be used to test the needle driver 100, such as for manufacturing purposes, quality assurance purposes, investigative purposes, or others.

The testing device 200 includes a frame 202, a plate 204, a plurality of levers 206, a shaft 212, a bracket 214, and a knob 216, any of which include a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The frame 202 defines a channel 208, which can be open (e.g., U-shape, V-shape, C-shape) or closed (e.g., D-shape, O-shape). The channel 208 hosts a tube 210 (e.g., cantileveredly, snugly). The tube 210 is hollow. The tube 210 can include a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others. The tube 210 contains the needle driver 100. For example, the needle driver 100 can be inserted into the tube 210 toward the channel 208.

The frame 202 hosts a plurality of structures 218. The structures 218 can include a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others. The structures 218 can be used for fastening or mating to a cover for the frame 202. The structures 218 can be used to engage (e.g., tension) the line 142 when the line 142 extends along the lateral channels 134 towards and away from the first jaw 102, the second jaw 104, the first set of teeth 140, the second set of teeth 140, the first roller 110, or the second roller 114). The channel 208 extends between the structures 218. The line 122 can extend over the channel 208. The line 142 can extend within the channel 208.

The plate 204 hosts a plurality of stops 220. The stops 220 engage with the levers 206 to limit travel thereof when the levers 206 are pressed in a direction towards the plate 204. The stops 220 can include a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The shaft 212 is rectilinear but can be non-rectilinear (e.g., sinusoidal, arcuate). The shaft 212 extends through the bracket 214. The shaft 212 has an end portion to which the knob 216 is mounted (or otherwise coupled). The bracket 214 is U-shaped, but can be shaped differently (e.g., C-shaped, L-shaped, J-shaped). As shown in FIG. 13, the shaft 212 is coupled to the first shaft 106 such that if the knob 216 is rotated, whether clockwise or counterclockwise, then that movement rotates or translates into rotation of the first shaft 106, which in turn drives the second shaft 108 based on the first set of teeth 140 driving the second set of teeth 120. For example, the knob 216 can be coupled to the first shaft 104 and the first shaft 104 is rotated via the knob 216. When pressed, the levers 206 can control which direction the shaft 212 rotates.

FIG. 14 shows a front view of an embodiment of a needle driver hosting a line according to this disclosure. Unlike FIGS. 1-9, the line 142 (red) extends along the first jaw 102 and over the second jaw 104 such that the line 142 extends between the first roller 110 and the first set of teeth 140. For example, the line 142 can extend along the first jaw 102 and over the second jaw 104 as distally as possible, although this feature can be omitted or modified (e.g., not distally as possible). This configuration increases or maximizes at least some leverage (and therefore at least some closing force of the second jaw 104) the line 142 can exert when moving the second jaw 104 to the closing position or closing the second jaw 104 shut. Further, this configuration allows the line 142 to act as a guard keeping at least some tissue out of reach of the first set of teeth 140 or the second set of teeth 120 behind the line 142. Resultantly, the line 142 can extend along the first jaw 102 and over the second jaw 104 when the second jaw 104 is in the closed position or the open position. The line 142 can extend between the first set of teeth 140 and the first roller 110, or the second set of teeth 120 and the second roller 114. The line 142 can extend along the first jaw 102 and over the second jaw 104 when the second jaw 104 is in the closed position and in the open position, where the line 142 extends between the first set of teeth 140 and the first roller 110 and between the second set of teeth 120 and the second roller 114.

Figure 15:
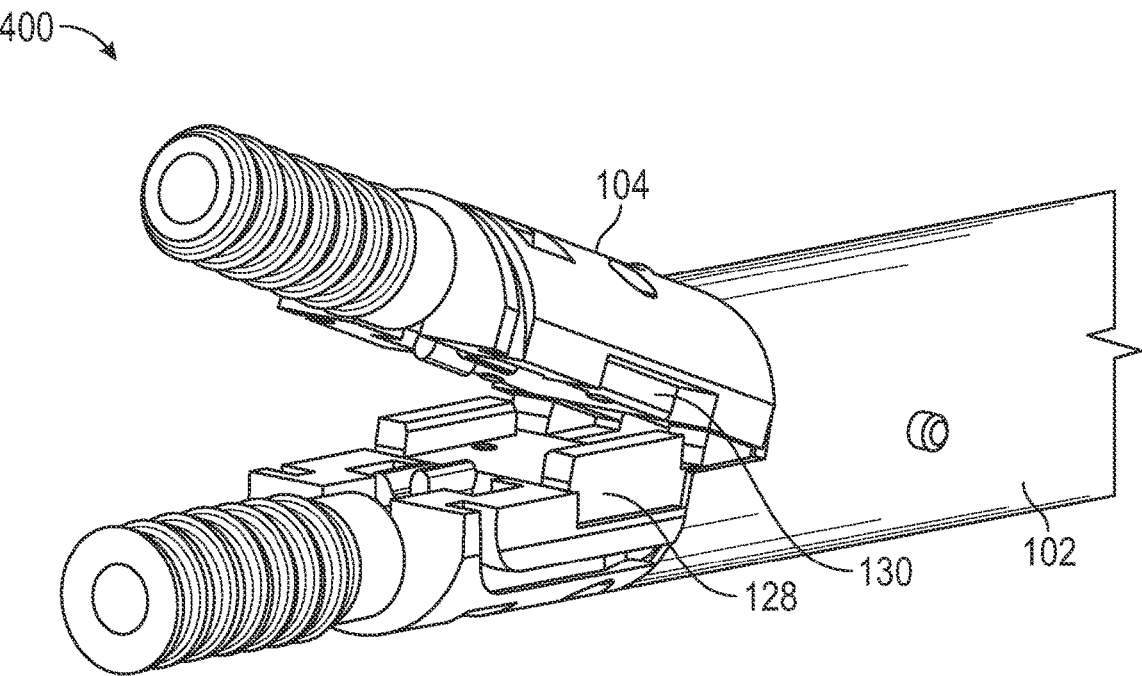
FIG. 15 shows a front view of an embodiment of a needle driver hosting a mating mechanism according to this disclosure.

FIG. 15 shows a front view of an embodiment of a needle driver hosting a mating mechanism according to this disclosure. Unlike FIGS. 1-9, the retaining block 128 is U-shaped and configured to receive (e.g., loosely, snugly)

the retaining block 130 when the second jaw 104 is in the closed position. This feature allows for a more robust and stable coupling of the first jaw 102 and the second jaw 104 when the second jaw 104 is in the closed position and minimizes jaw wobble, which may affect directional stability of the needle 144 while driving the needle 144. As such, the retaining block 128 can be hosted via the first jaw 102 and can include an enclosed area. The second retaining block 130 can be hosted via the second jaw 104. The retaining block 130 can be positioned within the enclosed area when the second jaw 104 is in the closed position. The enclosed area can be defined by the retaining block 128 when the retaining block is U-shaped.

Figure 16:
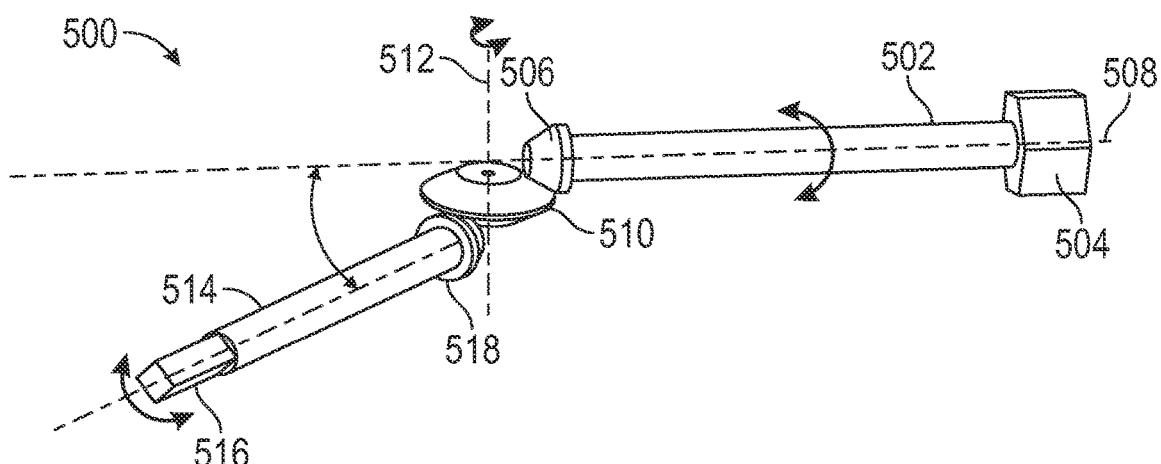
FIG. 16 shows a diagram of an embodiment of a bevel gear assembly for a needle driver according to this disclosure.
Figure 17:
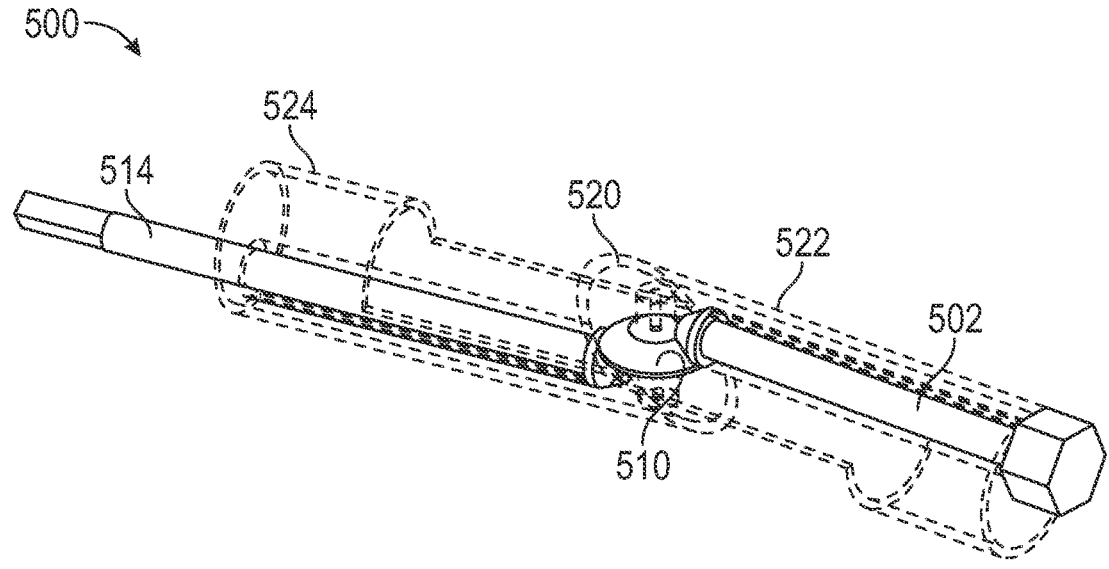
FIG. 17 shows a rear view of an embodiment of a needle driver hosting a bevel gear assembly according to this disclosure.
Figure 18:
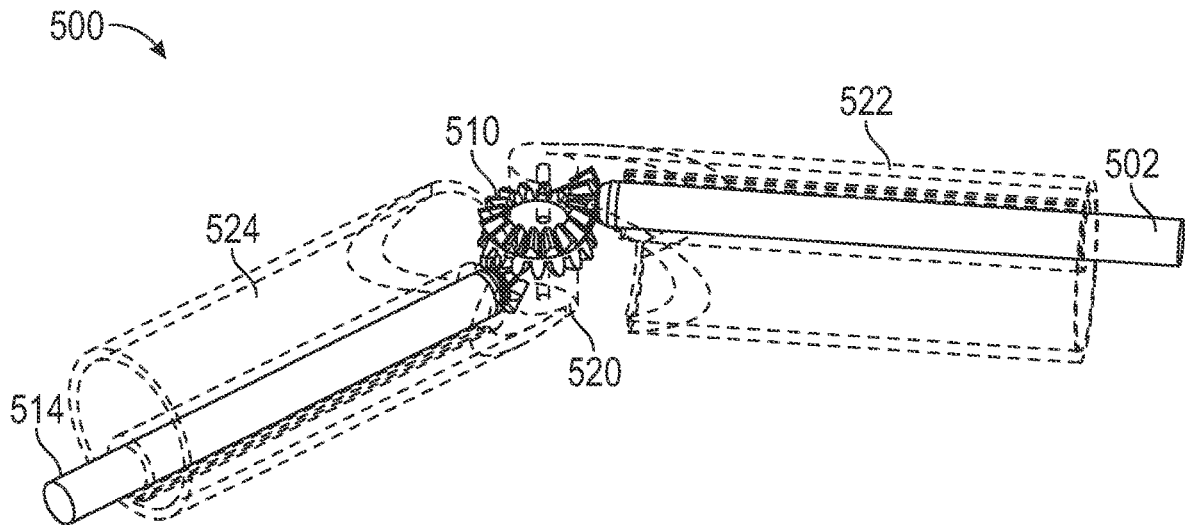
FIG. 18 shows a front view of an embodiment of a needle driver hosting a bevel gear assembly according to this disclosure.

FIG. 16 shows a diagram of an embodiment of a bevel gear assembly for a needle driver according to this disclosure. FIG. 17 shows a rear view of an embodiment of a needle driver hosting a bevel gear assembly according to this disclosure. FIG. 18 shows a front view of an embodiment of a needle driver hosting a bevel gear assembly according to this disclosure. In particular, a needle driver 500 includes a first shaft 502, a double faced bevel gear 510, and a second shaft 514. The first shaft 502 is housed within a first housing 522 (e.g., tube, frame, case). The second shaft 514 is housed within a second housing 524 (e.g., tube, frame, case).

The first shaft 502 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The first shaft 502 a proximal end portion hosting a handle 504 and a distal end portion hosting a first bevel gear 506, whether assembled therewith (e.g., fastened, mated) or unitary (e.g., monolithic, same material). The first shaft 502 can be rotated clockwise or counterclockwise about an axis 508. This rotation can be less than about 360 degrees or more than about 360 degrees. The first shaft 502 can be internally solid or hollow (e.g., to pass lines therethrough). The first shaft 502 can have a lateral cross-section that is circular, oval, square, or others.

The second shaft 514 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The second shaft 514 has a proximal end portion hosting a second bevel gear 518, whether assembled therewith (e.g., fastened, mated) or unitary (e.g., monolithic, same material), and a distal end portion 516 hosting the first jaw 102 and the second jaw 104. The second shaft 514 can be internally solid or hollow (e.g., to pass lines therethrough). The second shaft 514 can have a lateral cross-section that is circular, oval, square, or others.

The first housing 522 or the second housing 524 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The double faced bevel gear 510 has a first face (e.g., upper) meshing with the first bevel gear 506 and a second face (e.g., lower) meshing with the second bevel gear 518. The first face opposes the second face. The double faced bevel gear 510 rotates about an axis 512, which is nonparallel to the axis 508. For example, the axis 508 is perpendicular to the axis 512.

The double faced bevel gear 510 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

As shown in FIGS. 16-18, when the first shaft 502 is rotated about the axis 508, whether clockwise or counterclockwise, the first bevel gear 506 rotationally meshes with the first side of the double faced bevel gear 510. This rotational meshing enables the double faced bevel gear 510 to rotate about the axis 512 and thereby enable the second side of the double faced bevel gear 510 to rotationally mesh with the second bevel gear 518. Resultantly, the second shaft 514 can move relative to the first shaft 502 or the double faced bevel gear 510 about the axis 512. Therefore, when a user is holding the first housing 522 and rotating the first shaft 502 along the axis 508, then the double faced bevel gear 510 causes the second shaft 514 to rotate about the axis 512. Since the second shaft 514 is secured (e.g., fastened, mated, interlocked, adhered) to the second housing 524, then this configuration causes the second housing 524 to move relative to the first housing 522 about the axis 512. Resultantly, the first housing 522 can host the first shaft 502 equipped with the first bevel gear 506. The second housing 524 can host the first jaw 102, the second jaw 104, and the second shaft 514 equipped with the second bevel gear 518 distal to the first roller 110 and the second roller 114. The first bevel gear 506 and the second bevel gear 518 can engage a third bevel gear such that the second housing 524 can move relative to the first housing 522 based on the first shaft 502 being rotated about the axis 508. The third bevel gear can be the double faced bevel gear 510 having the first side and the second side, where the first side opposes the second side. Consequently, the first side engages the first bevel gear 506 and the second side engages the second bevel gear 518 such that the second housing 524 can move relative to the first housing 522 based on the first shaft 502 being rotated about the axis 508.

The second housing 524 can move relative to the first housing 522 based on the double faced bevel gear 510 functioning as a pivot point 520. As such, the first housing 522 and the second housing 524 are structured accordingly so that when the first housing 522 and the second housing 524 are rectilinearly positioned relative to each other, then there is a relatively seamless or flush transition therebetween. For example, as shown in FIG. 17, the first housing 522 and the second housing 524 can have corresponding adjacent end portions complementing or supplementing each other in shape. However, note that this feature is absent in FIG. 18.

FIG. 19 shows a diagram of an embodiment of a side profile of a pair of rollers engaging an arcuate needle according to this disclosure. The needle 144 can be of a RB-1 type and is positioned between the first roller 110 and the second roller 114. As such, this configuration approximates a groove design guidance accept for a reversed rake as flat on needle faces away from the proximal end of needle driver 100. The needle 144 is shown in parallel forward facing and perpendicular downward facing positions. Perpendicular upward facing is possible. Note that the needle 144 can be of a non RB-1 type. For example, the needle 144 can be any type of cuticular needle, plastic/cosmetic needle, orthopedic needle, endoscopic needle, general surgery needle, microsurgery needle, cardiovascular needle, ophthalmic needle, or any other type, size, shape, taper, leading point, trailing point, material, suture gauge, taper point, trocar point, blunt point, sternum point, short cutting tip, precision point, micropoint, reverse cutting type, straight cutting type, circle heavy type, lancet type, eyed, or others.

FIG. 20 shows a diagram of an embodiment of a side profile of a pair of rollers engaging an arcuate needle according to this disclosure. Unlike FIG. 19, the needle 144 can be of a SH type. The needle 144 is shown in parallel forward facing and perpendicular downward facing positions. Perpendicular upward facing is possible. Note that the needle 144 can be of a non SH type. For example, the needle 144 can be any type of cuticular needle, plastic/cosmetic needle, orthopedic needle, endoscopic needle, general surgery needle, microsurgery needle, cardiovascular needle, ophthalmic needle, or any other type, size, shape, taper, leading point, trailing point, material, suture gauge, taper point, trocar point, blunt point, sternum point, short cutting tip, precision point, micropoint, reverse cutting type, straight cutting type, circle heavy type, lancet type, eyed or others.

FIG. 21 shows a pair of diagrams of a pair of embodiments of a pair of side profiles of a pair of rollers engaging a pair of arcuate needles of a pair of different sizes according to this disclosure. Regarding the needle 144, note that at least some free space around the RB-1 needle 144 is due to compromises required to allow the SH needle 144 to fit same grooves. Stability of either needle 144 in these grooves is possible. Note that the needle 144 can be of a non SH type or a non RB-1 type. For example, the needle 144 can be any type of cuticular needle, plastic/cosmetic needle, orthopedic needle, endoscopic needle, general surgery needle, microsurgery needle, cardiovascular needle, ophthalmic needle, or any other type, size, shape, taper, leading point, trailing point, material, suture gauge, taper point, trocar point, blunt point, sternum point, short cutting tip, precision point, micropoint, reverse cutting type, straight cutting type, circle heavy type, lancet type, eyed or others.

Figures 22, 23:
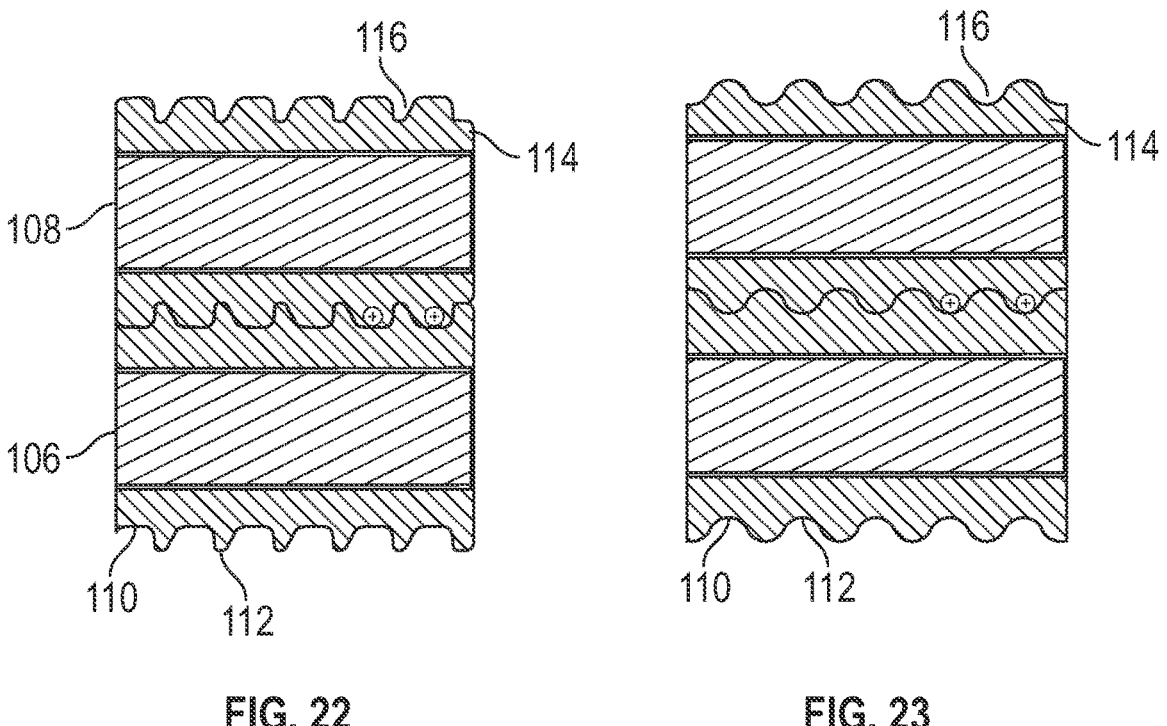
FIG. 22 shows a diagram of an embodiment of a side profile of a roller having a plurality of slanted grooves according to this disclosure.
FIG. 23 shows a diagram of an embodiment of a side profile of a roller having a plurality of wave grooves according to this disclosure.

FIG. 22 shows a diagram of an embodiment of a side profile of a roller having a plurality of slanted grooves according to this disclosure. The first roller 110 and the second roller 114 are shown with sutures 2-0 and 0 in cross section. When tying sutures, even though at least some "hooked" grooves along bottom of the first roller 110 could theoretically snag sutures, these are still usable. Note that sutures can be non 2-0 and 0 in cross-section. For example, sutures can be 6-0 or any other size defined by United States Pharmacopeia. For example, suture can be any suture from #7 to #10-0, whether collagen (or another material) or synthetic (or natural).

FIG. 23 shows a diagram of an embodiment of a side profile of a roller having a plurality of wave grooves according to this disclosure. The first roller 110 and the second roller 114 are shown with sutures 2-0 and 0 in cross section. Rounded wave grooves could prove to be less likely to snag sutures during tying process. Note that sutures can be non 2-0 and 0 in cross-section. For example, sutures can be 6-0 or any other size defined by United States Pharmacopeia. For example, suture can be any suture from #7 to #10-0, whether collagen (or another material) or synthetic (or natural).

Figure 24:
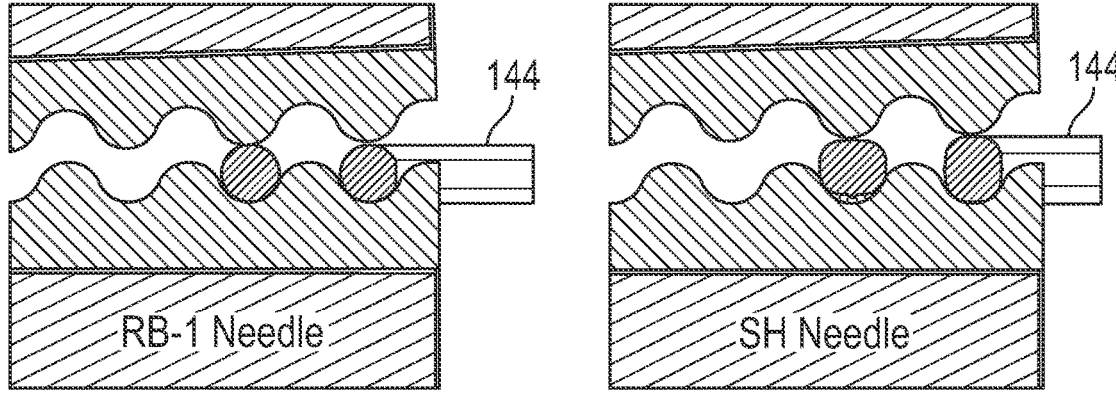
FIG. 24 shows a pair of diagrams of a pair of embodiments of a pair of side profiles of a pair of rollers with a plurality of wave grooves engaging a pair of arcuate needles of a pair of different sizes according to this disclosure.

FIG. 24 shows a pair of diagrams of a pair of embodiments of a pair of side profiles of a pair of rollers with a plurality of wave grooves engaging a pair of arcuate needles of a pair of different sizes according to this disclosure. The first roller 110 and the second roller 114 are shown with RB-1 and SH needles 144. The RB-1 needle 144 runs low in bottom of groove as does the SH needle 144 when parallel to the first jaw 102 or the second jaw 104. The SH needle 144 runs high in groove when oriented perpendicular to the first jaw 102 or the second jaw 104 due of its larger, oval, cross section. Stability of either needle 144 in this groove is possible. Note that the needle 144 can be of a non SH type or a non RB-1 type. For example, the needle 144 can be any type of cuticular needle, plastic/cosmetic needle, orthopedic needle, endoscopic needle, general surgery needle, micro-surgery needle, cardiovascular needle, ophthalmic needle, or any other type, size, shape, taper, leading point, trailing point, material, suture gauge, taper point, trocar point, blunt point, sternum point, short cutting tip, precision point, micropoint, reverse cutting type, straight cutting type, circle heavy type, lancet type, eyed or others.

Figure 25:
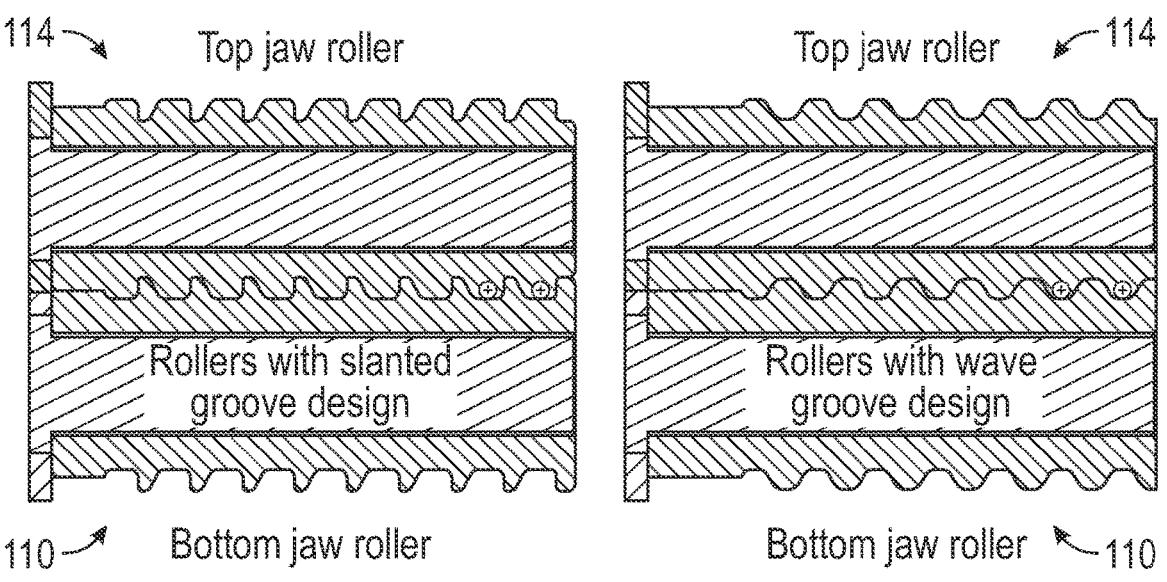
FIG. 25 shows a pair of diagrams of a pair of embodiments of a pair of side profiles of a pair of rollers with a pair of different groove designs engaging a pair of arcuate needles of a pair of different sizes according to this disclosure.

FIG. 25 shows a pair of diagrams of a pair of embodiments of a pair of side profiles of a pair of rollers with a pair of different groove designs engaging a pair of arcuate needles of a pair of different sizes according to this disclosure. These are two different sets of rollers with groove designs that would allow driving the needle 144 and grasping a suture (no gap between the first roller 110 and the second roller 114). Note that the rollers 110, 114 in the second jaw 102 and the first jaw 104 of each set are asymmetrical (although symmetrical is possible), meaning that a shape of the second roller 114 is not identical to the first roller 110, but rather complimentary in shape to fill at least some space. The slanted groove rollers could have two variations, one with the slanted wall of the groove slanting backwards (as in the left-sided drawing) or slanted forward as shown in FIG. 26.

Figure 26:
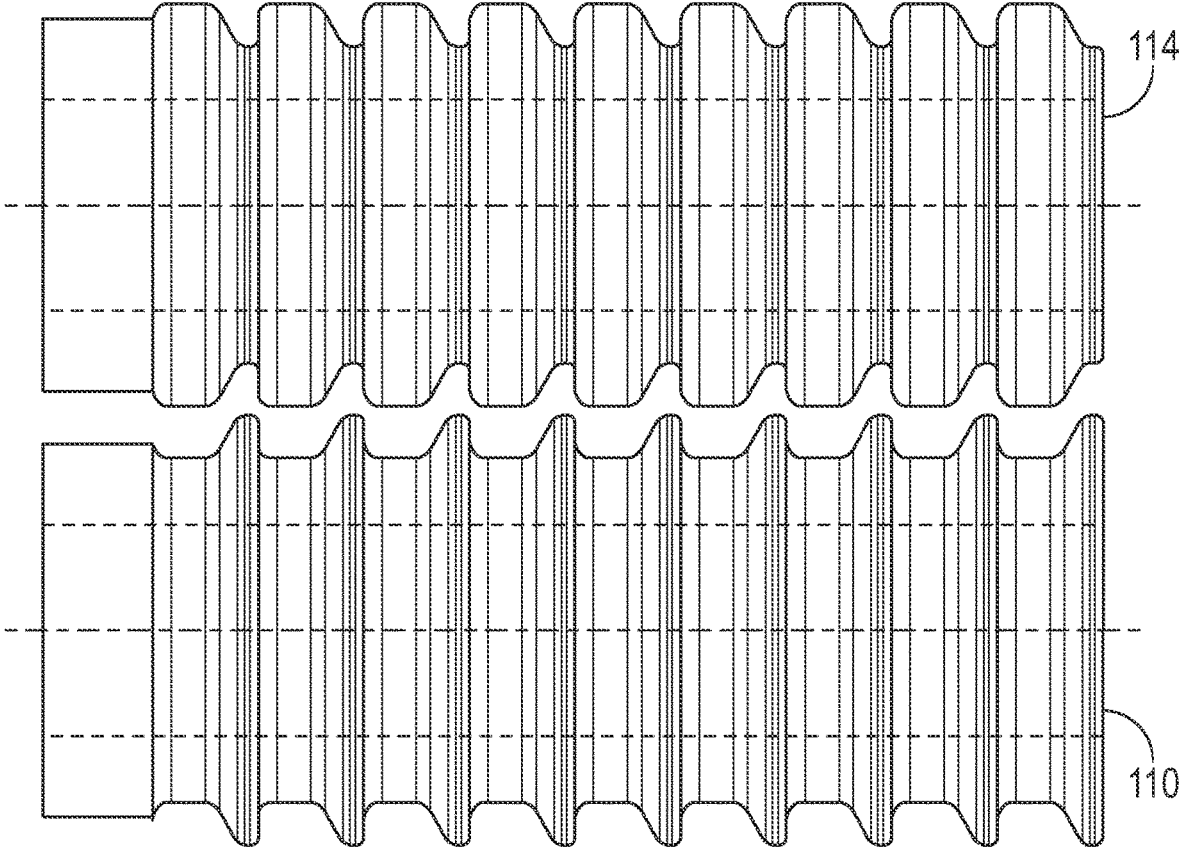
FIG. 26 shows a diagram of an embodiment of a pair of rollers with a slanted groove design according to this disclosure.

FIG. 26 shows a diagram of an embodiment of a pair of rollers with a slanted groove design according to this disclosure. Note that the slanted wall of the groove is slanted forward (rollers are pointing to the right) and the flat wall is on the back part of each groove.

As shown in FIGS. 19-26, the first roller 110 can host a plurality of slanted grooves. The slanted grooves can be slanted in a direction away from the first set of teeth 140. The slanted grooves can be slanted in a direction toward the first set of teeth 140. The first roller 110 can host a plurality of wavy grooves. Likewise, the second roller 114 can host a plurality of slanted grooves. The slanted grooves can be slanted in a direction away from the second set of teeth 120. The slanted grooves can be slanted in a direction toward the second set of teeth 120.

Figure 27:
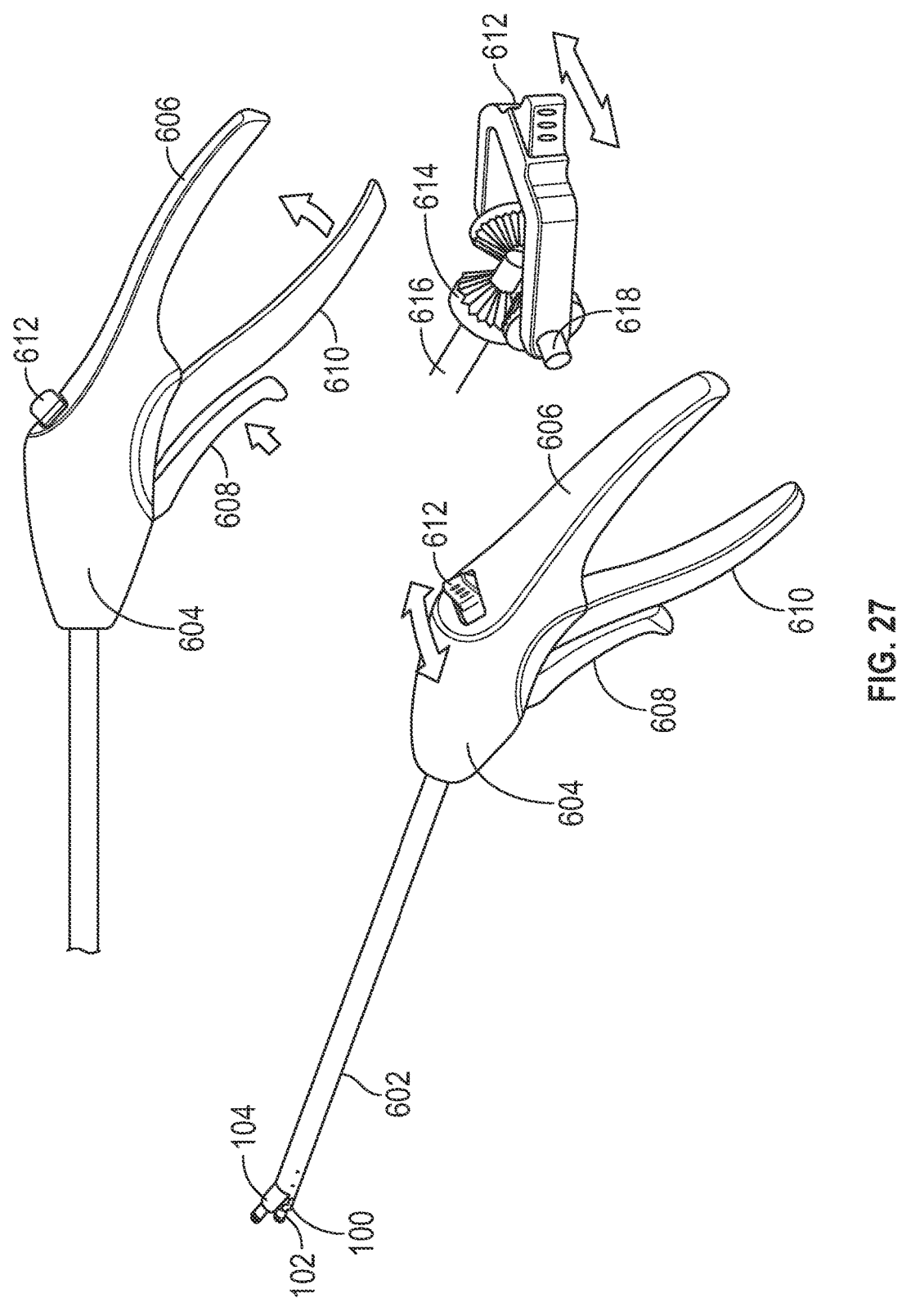
FIG. 27 shows a rear view of an embodiment of a needle driver with a plurality of levers according to this disclosure.
Figure 28:
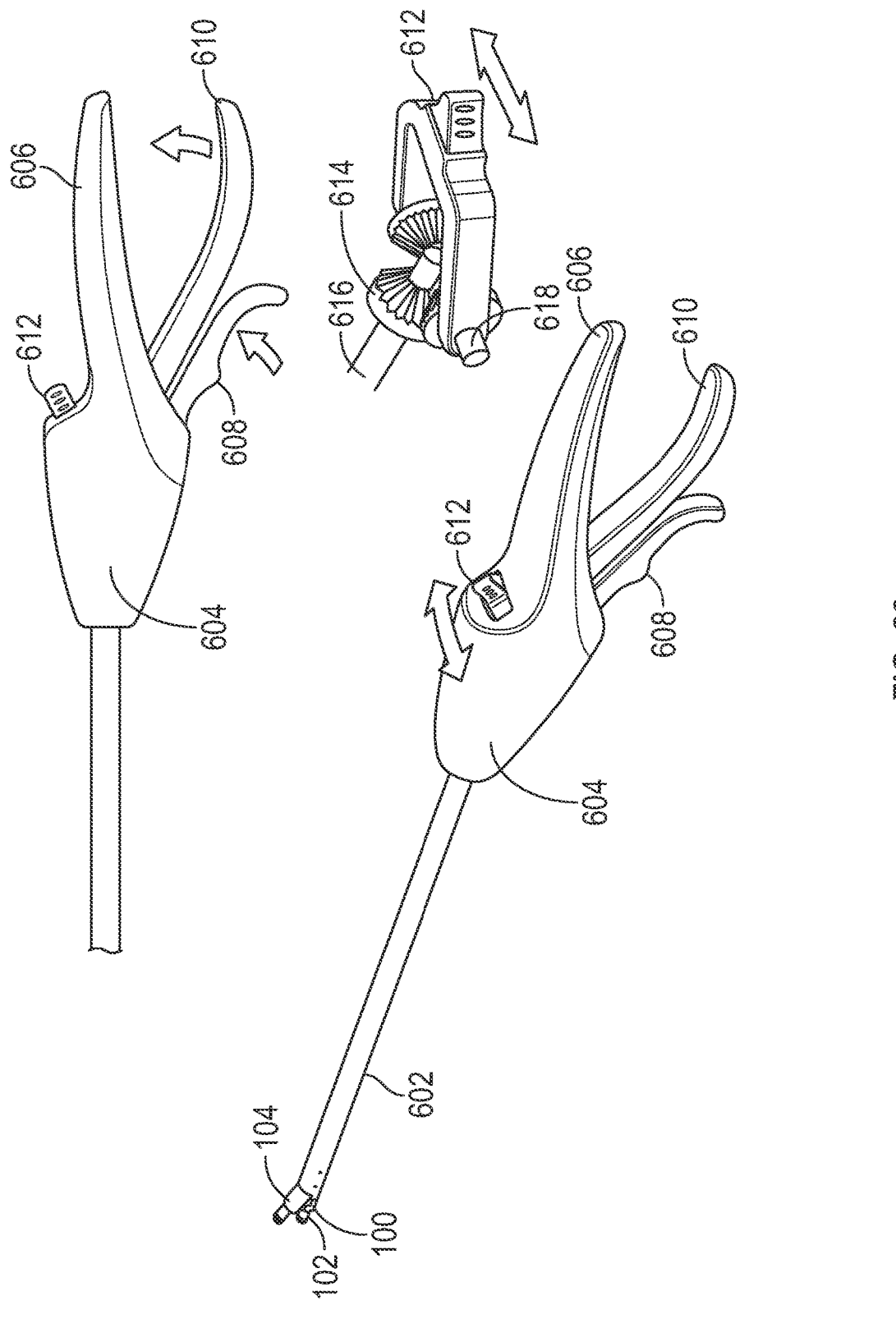
FIG. 28 shows a rear view of an embodiment of a needle driver with a plurality of levers according to this disclosure.

FIG. 27 shows a rear view of an embodiment of a needle driver with a plurality of levers according to this disclosure. FIG. 28 shows a rear view of an embodiment of a needle driver with a plurality of levers according to this disclosure. In particular, a needle driver 600 includes a tube 602 having a distal end portion hosting the needle driver 100 inclusive of the first jaw 102 and the second jaw 104. The tube 602 has a lateral cross-section of a circle, but this shaping can vary (e.g., oval, square, triangle, rectangle, pentagon, octagon). The tube 602 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The needle driver 600 includes a housing 604 hosting a handle 606, a first lever 608, and a second lever 610, any of which includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The tube 602 longitudinally extends from the housing 604 such that the first jaw 102 and the second jaw 104 are distal to the housing 604. The first lever 608 (rotational driver) rotationally drives the first shaft 106 of the first jaw 102, whether clockwise or counterclockwise, as explained above. For example, the first lever 608 can be iteratively or repeatedly pressed or released, as needed, similar to a trigger of a firearm. The second lever 610 (clamp lever) moves the second jaw 104 relative to the first jaw 102 between the open position and the closed position, as explained above. For example, the second lever 610 can be iteratively or repeatedly pressed or released, as needed, similar to a parking handbrake lever in a car. The first lever 608 is movable relative to the handle 606, whether towards or away therefrom. The second lever 610 is movable relative to the handle 606, whether towards or away therefrom.

The housing 604 hosts a switch 612, a shaft 616, a first bevel gear 618 (right side), a second bevel gear 618 (left side), and a third bevel gear 614 (central), any of which includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The shaft 616 hosts the third bevel gear 614. Although the shaft 616 has a proximal end portion that hosts the third bevel gear 614, this configuration can vary where the shaft 616 can host the third bevel gear 614 not at the proximal end portion, but another portion thereof, which can be a medial or a non-medial portion of the shaft 616.

The first bevel gear 618 and the second bevel gear 618 are rotationally mounted onto the switch 612 such that the first bevel gear 618 and the second bevel gear face each other or oppose each other, while avoiding contact with each other. The switch 612 is U-shaped or C-shaped, but can be shaped differently (e.g., rotary). The switch 612 hosts a projection to enable a user to selectively move the switch 612 between a first lateral position and a second lateral position. For example, the switch 612 can be either at the first position or at the second position, but not both. With the projection, the switch 612 is Y-shaped, but can be shaped differently, such as when the projection is absent. The tube 602 has a longitudinal axis, the switch 612 moves lateral to the longitudinal axis. However, this movement can vary (e.g., longitudinal, parallel, arcuate, circular), which can depend on what type of the switch 612 is used.

In the first lateral position, the switch 612 moves the first bevel gear 618 to enable the first bevel gear 618 to mesh with the third bevel gear 614 and avoid the third bevel gear 614 meshing with the second bevel gear 618. Note that this configuration can be reversed where instead of the first bevel gear 618 being moved by the switch 612, the third bevel gear 614 can be moved by the switch 612 to enable the first bevel gear 618 to mesh with the third bevel gear 614 and avoid the third bevel gear 614 meshing with the second bevel gear 618. For example, the shaft 616 can be moved.

In the second lateral position, the switch 612 moves the second bevel gear 618 to enable the second bevel gear 618 to mesh with the third bevel gear 614 and avoid the third bevel gear 614 meshing with the first bevel gear 618. Note that this configuration can be reversed where instead of the second bevel gear 618 being moved by the switch 612, the third bevel gear 614 can be moved by the switch 612 to enable the second bevel gear 618 to mesh with the third bevel gear 614 and avoid the third bevel gear 614 meshing with the first bevel gear 618. For example, the shaft 616 can be moved.

As shown in FIGS. 27-28, the first bevel gear 618 or the second bevel gear 618 can selectively engage the third bevel gear 616 based on how the switch 612 is positioned. For example, the third bevel gear 616 enables the first set of teeth 140 of the first jaw 102 to drive the second set of teeth 140 of the second jaw 104. The first bevel gear 618 rotates the shaft 616 in a first direction (e.g., clockwise, counterclockwise). The second bevel gear 618 rotates the shaft 616 in a second direction (e.g., clockwise, counterclockwise). The first direction is different (e.g., opposite) from the second direction. The switch 612 moves between the first position and the second position, where the first position corresponds to the first direction and the second position corresponds to the second direction. For example, the first direction can be clockwise and the second direction can be counterclockwise.

Figures 29, 30:
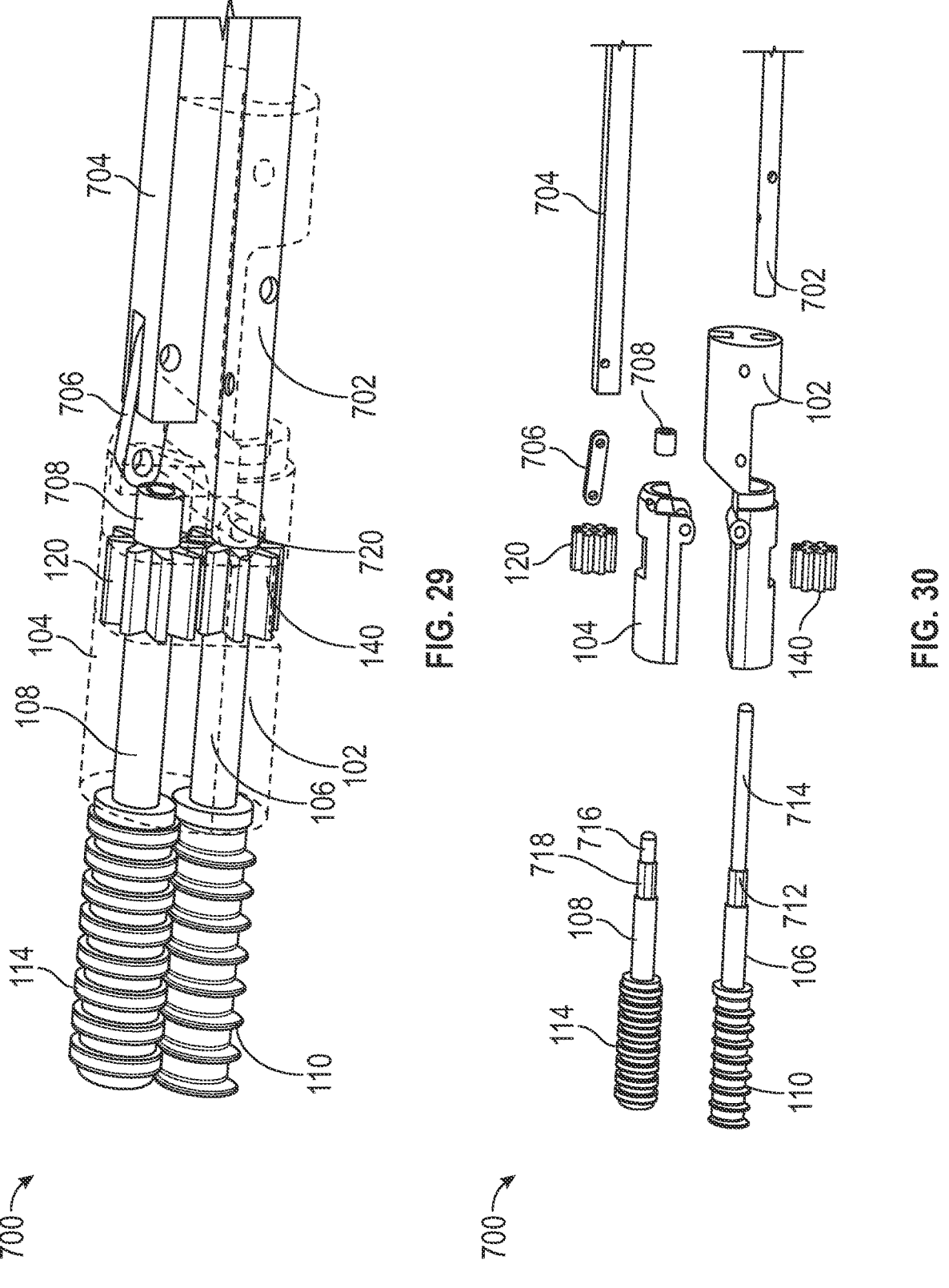
FIG. 29 shows a rear view of an embodiment of a needle driver with a linkage according to this disclosure.
FIG. 30 shows an exploded view of an embodiment of a needle driver with a linkage according to this disclosure.

FIG. 29 shows a rear view of an embodiment of a needle driver with a linkage according to this disclosure. FIG. 30 shows an exploded view of an embodiment of a needle driver with a linkage according to this disclosure. A needle driver 700 contrasts with the needle driver of FIGS. 1-15 in various ways.

The first shaft 106 is unitary (e.g., monolithic, same material) with the first roller 110. The first shaft 106 has a proximal end portion 714 distal to the first roller 110. The first shaft 106 hosts a first teethed interface 712 between the first roller 110 and the proximal end portion 714. The first teethed interface 712 is unitary to the first shaft 106 (e.g., monolithic, same material), but can be coupled to the first shaft 106 in other ways (e.g., mounted, fastened, adhered, mated, interlocked). Although the first shaft 106 steps down from the first roller 110 to the proximal end portion 714, this configuration can be omitted or modified and the first shaft 106 can avoid stepping down or can step up from the first roller 110 to the proximal end portion 714.

The first teethed interface 712 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The second shaft 108 is unitary (e.g., monolithic, same material) with the second roller 114. The second shaft 108 has a proximal end portion 716 distal to the second roller 114. The second shaft 108 hosts a second teethed interface 718 between the second roller 114 and the proximal end portion 716. The second teethed interface 718 is unitary to the second shaft 108 (e.g., monolithic, same material), but can be coupled to the second shaft 108 in other ways (e.g., mounted, fastened, adhered, mated, interlocked). Although the second shaft 108 steps down from the second roller 114 to the proximal end portion 716, this configuration can be omitted or modified and the second shaft 108 can avoid stepping down or can step up from the second roller 110 to the proximal end portion 716.

The second teethed interface 718 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The second shaft 108 hosts a collar 708. The collar 708 has a lateral cross-section of a circle, but this can vary (e.g., oval, square, octagon, pentagon, rectangle, triangle). The collar 708 is internally hollow, smooth or rough, and sized such that the proximal end portion 716 of the second shaft 108 can be inserted into the collar 720, whether freely or snugly. When the proximal end portion 716 of the second shaft 108 is externally threaded and the collar 708 is internally threaded, then the proximal end portion 716 can thread into the collar 708. As such, the second shaft 108 can host the collar 708 such that the second set of teeth 120 is positioned between the second roller 114 and the collar 708 when the collar 708 receives the proximal end portion 716 of the second shaft 108. Although the collar 708 is open on both end portions, this can vary where the collar 706 is open on only one end portion that receives the proximal end portion 716 of the second shaft 108. For example, the collar 708 can be a cap. As such, the collar 708 can extend about the second shaft 108 such that the second set of teeth 120 is positioned between the second roller 114 and the collar.

The collar 708 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The first set of teeth 140 is embodied as a first gear wheel. The first gear wheel defines a first interior channel having a first teethed interior surface configured to engage with the first teethed interface 712. As such, when the first gear wheel is mounted onto the first shaft 106, the first teethed interior surface meshes with the first teethed interface 712 and the first gear wheel is correspondingly rotated when the first shaft 106 is rotated.

The second set of teeth 120 is embodied as a second gear wheel. The second gear wheel defines a second interior channel having a second teethed interior surface configured to mesh with the second teethed interface 718. As such, when the second gear wheel is mounted onto the second shaft 108, the second teethed surface engages with the second teethed interface 718. Therefore, when the first gear wheel rotates and thereby rotates the second gear wheel, this movement causes the second teethed interior surface of the second gear wheel to mesh with the second teethed interface 718 and thereby rotate the second shaft 108. For example, the first set of teeth 140 can be mounted in the first gear wheel and the first shaft 106 can be teethed such that the first shaft 106 engages the gear wheel. The second set of teeth 120 can be mounted in a second gear wheel and the second shaft 108 is teethed such that the second shaft 108 engages the second gear wheel.

The second jaw 104 is pivotably coupled to the first jaw 102 via a pin 720. The pin 720 is rectilinear, but can be non-rectilinear (e.g., arcuate, sinusoidal). The pin 720 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others. As such, the second jaw 104 can move relative to the first jaw 102 between the open position and the closed position based on pivoting about the pin 720.

The proximal end portion 714 of the first shaft 106 is inserted into the first jaw 102 and, internal to or external from the first jaw 102, is inserted into a third shaft 702. For example, the third shaft 702 can be used to drive the first shaft 106, which can be when the first jaw 102 hosts the third shaft 702. The third shaft 702 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The third shaft 702 has a lateral cross-section that is circular, but this can vary (e.g., square, oval, triangular). The third shaft 702 is hollow and has an interior surface, which can be rough or smooth. As such, the proximal end portion 714 of the first shaft 106 can freely or snugly remain within the third shaft 702. Note that this configuration can be reversed and the third shaft 702 can be inserted into the first shaft 106. For example, the third shaft 702 can extend into the first shaft 106, where the third shaft 702 drives the first shaft 106 and the first jaw 102 hosts the third shaft 702.

The second jaw 104 is coupled to a distal end portion of a link 706. This coupling can be pivotal, hinged, or others. For example, the second jaw 104 can couple to the distal end portion of the link 706 via a pin such that the second jaw 104 can move between the closed position and the open position based on pivoting about the pin. Although the link 706 is shown a plate, this configuration can vary and the link 706 can be embodied differently (e.g., clip, bracket).

The link 706 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The link 706 has a proximal end portion coupled to a bar 704. The bar 704 has a cross-section of an I-beam, but this can vary (e.g., T-shape, L-shape, J-shape, U-shape, D-shape, O-shape). The bar 704 is solid, but can be hollow. The bar 704 can be hosted (e.g., supported, suspended, mounted, fastened, interlocked, mated) via the first jaw 102 or the second jaw 104.

The bar 704 includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The proximal end portion of the link 706 is coupled to the bar 704 in various ways, such as pivotal, hinged, or others. For example, the proximal end portion of the bar 704 can couple to the link 706 via a pin such that the link 706 can move in accordance with the second jaw 104 moving between the closed position and the open position based on the link 706 pivoting about the pin.

The proximal end portion of the bar 704 is coupled to a control interface. The proximal end portion of the bar 704 can be coupled to the control interface in various ways (e.g., linkage, fastening, mating, interlocking, adhering, hooked). As such, the bar 704 functions similarly to the line 122 or the line 144. For example, when the bar 704 is pulled in a direction away from the second roller 114, the second shaft 108, the second set of teeth 120, or the sleeve 708 via the control interface, then the second jaw 104 can be moved from the closed position to the open position. Likewise, when the bar 704 is pushed in a direction towards the second roller 114, the second shaft 108, the second set of teeth 120, or the sleeve 708 via the control interface, then the second jaw 104 can be moved from the open position to the closed position. Note that the bar 704 can be replaced with a cable or another form of a line, as explained above.

The control interface can be a manual interface or an automated interface. For example, the manual interface can include a user input device (e.g., trigger, button, switch, dial, lever). For example, the automated interface can include a mover (e.g., motor, engine, actuator, mechanical linkage, gear mechanism, pulley mechanism, hydraulic mechanism, pneumatic mechanism). For example, the automated interface can be included in a robot (e.g., articulating arm, single or multi-joint end effector). For example, the needle driver 700 can include a distal portion hosting the first jaw 102 and the second jaw 104 and a proximal portion hosting the control interface. For example, the end effector can host (e.g., support, suspend, fasten, mate, interlock) the first jaw 102 or the second jaw 104. For example, the first jaw 102 and the second jaw 104 can be housed in a housing (e.g., tube, case, encasement, arm). For example, the housing includes a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

As shown in FIGS. 29-30, the link 706, which can be a plate, can be coupled to the bar 704 and the second jaw 104, where the second jaw 104 moves relative to the first jaw 102 between the closed position and the open position based on the bar 704 being moved along the first jaw 102. The second jaw 104 can move from the closed position to the open position based on the bar 704 moving away from the first set of teeth 140. The second jaw 104 can move from the open position to the closed position based on the bar 704 moving toward the first set of teeth 140. The link 706 can cause the second jaw 104 to move between the closed position and the open position based on the bar 704 being moved along the first jaw 102. The third shaft 702 can receive the first shaft 106, where the third shaft 702 can drive the first shaft 106 and the bar 704 can move along the third shaft 704, while the first jaw 102 hosts the third shaft 702. The third shaft 702 can extend into the first shaft 106, where the third shaft 702 drives the first shaft 106 and the bar 704 moves along the third shaft 702, while the first jaw 102 hosts the third shaft 704.

Therefore, as shown in FIGS. 29-30, the first roller 110 and the first shaft 106 can be unitary (e.g., monolithic, same material) and the second roller 114 and the second shaft 108 are unitary (e.g., monolithic, same material). The first set of teeth 140 and the second set of teeth 120 can be embodied as spur gears that are mounted to shaft ends and retained with the collar 720, which can be welded-on. Therefore, unlike FIGS. 1-15, no retaining plate or screws can be required. The jaw hinge pin 720 can be more robust than slip join design (e.g., male/female of FIGS. 1-15). The push/pull bar 704 with the link 706 can actuates the second jaw 104 relative to the first jaw 102. In contrast to FIGS. 1-15, loss of at least some cables can simplify actuation trigger mechanism or can free-up handle internal space, potentially leaving more room for rotation drive mechanism.

FIG. 31 shows a diagram of a side profile of a roller according to this disclosure. In particular, a roller 800 can be configured as any other roller described herein. The roller 800 has a plurality of grooves, which can be microgrooves, that are configured (e.g. sized, dimensioned, structured) to allow grasping of both a needle and its suture thread due to a small size of the grooves or a shallow depth of the grooves. Unlike some rollers described above where the grooves are staggered with crests/ridges of the grooves in one roller fitting into troughs of the grooves in opposing roller, the grooves of the roller 800 revert back to a parallel orientation in which the grooves in one roller align symmetrically with the grooves in opposing roller, but leaving a gap so small therebetween that would not only allow the rollers to grasp a needle therebetween but would also allow the suture thread to be grasped between the rollers even if the suture thread fell in a space between the grooves. Note that although FIG. 8 shows various sizes, dimensions, and angles, the roller 800 is not limited to any of these shown values and, for any shown value, the roller 800 can vary in sizes, dimensions, and angles (e.g. greater, lesser, remain same).

As shown in FIGS. 1-31, the first shaft 106 can extend into the first jaw 102 or can avoid extending into the second jaw 104. The first shaft 106 can extend out of the first jaw 102 on two opposing sides thereof. The first shaft 106 can cantileveredly extend out of the first jaw 102. Likewise, the second shaft 108 can extend into the second jaw 104 or can avoid extending into the first jaw 102. The second shaft 108 can extend out of the second jaw 104 on only one side thereof. The second shaft 108 cantileveredly extends out of the second jaw 104. The first shaft can 106 avoid contacting the second shaft 108 when the second jaw 104 is in the closed position. The first shaft 106 can avoids contacting the second shaft 108 when the second jaw 104 is in the open position. The first roller 110 and the first set of teeth 140 can be spaced apart from each other on the first shaft 106. The second roller 114 and the second set of teeth 120 can be spaced apart from each other on the second shaft 108. For example, the first roller 110 and the first set of teeth 140 can be spaced apart from each other on the first shaft 106 to define a first distance (e.g., less than 1 inch) therebetween and the second roller 114 and the second set of teeth 120 can be spaced apart from each other on the second shaft 108 to define a second distance (e.g., less than 1 inch) therebetween. The first distance can be greater than, equal to, or lesser than the second distance.

A needle driver, as shown in FIGS. 1-31, can be a multifunctional device that is able to function as a needle driver, a grasper, or a dissector. The multifunctional device can drive needle of various sizes, in a multiplicity of angles, which can, in certain cases, be up to about 310 degrees about a long axis of the multifunctional device. The multifunctional device can also be used as a grasper and dissector. The multifunctional device can be used to enable faster recovery time, increased patient convenience, reducing suturing time, reduce patient and surgeon discomfort, smaller blood loss, or others. The multifunctional device can be an intuitive, easy to use, and versatile suturing technology that mimics traditional suturing devices surgeons are commonly trained with. The multifunctional device can integrate tips allowing users to grasp or rotate a curved surgical needle without requiring rotational motion at a user's wrist. The multifunctional device can enable a bi-directional motion or manipulation of the needle for easier, more convenient or safer handling. For example, a needle driver, as shown in FIGS. 1-31, can simplify suturing based on enhancing surgeons' suturing capabilities with minimal device specific training, enables easy transfer of skills from open to minimally invasive surgery, and decreasing time and need for instrument exchange with the needle driver's versatile multifunctional capabilities.

A needle driver, as shown in FIGS. 1-31, can include a counter (e.g., mechanical, mechatronic, electronic, analog, digital, chemical reaction) to count how many times the first shaft 106 or the second shaft 106 have been rotated, how many times the second jaw 104 has moved relative to the first jaw 102 from the open position to the closed position (or vice versa), how many times the needle driver has undergone a sterilization procedure (e.g. hot steam, autoclave), or how many times a lever (e.g., rotation, clamp) has been pulled. For example, this can be a physical or chemical process that causes a change, which can be a cumulative change, in a measurable way to assess the number of times the needle driver has been used in accordance with use instructions. The counter can be of odometer-type, digital display type, color-type, scale-type, or others.

A needle driver, as shown in FIGS. 1-31, can be used to perform a method. The method can include causing a device (e.g., needle driver) to be inserted into a first object (e.g., animate, inanimate, human, animal, mannequin, doll). The device includes the first jaw 102 hosting the first shaft 106 and the second jaw 104 hosting the second shaft 108. The first shaft 106 hosts the first roller 110 and the first set of teeth 140. The second shaft 108 hosts the second roller 114 and the second set of teeth 120. The second jaw 104 moves relative to the first jaw 102 between an open position and a closed position. The first set of teeth 140 meshes with the second set of teeth 120 when the second jaw 104 is in the closed position such that (a) the first set of teeth 140 can drive the second set of teeth 120 and (b) the first roller 110 and the second roller 114 can drive a needle therebetween when the first set of teeth 140 drives the second set of teeth 120. The method can include acting with the device. An example of such acting can include causing the first roller 110 and the second roller 114 to grasp a second object (e.g., animate, inanimate, tissue, organ, body part, implantable, wearable, surgical instrument) therebetween within the first object when the second jaw 104 is in the closed position. An example of such acting can include causing the first roller 110 and the second roller 114 to manipulate the second object within the first object when the second jaw 104 is in the closed position. An example of such acting can include causing the first roller 110 and the second roller 114 to dissect the second object within the first object when the second jaw 104 is in the closed position. An example of such acting can include causing the first roller 110 and the second roller 114 to isolate the second object within the first object when the second jaw 104 is in the closed position. An example of such acting can include causing the first roller 110 and the second roller 114 to separate the second object within the first object when the second jaw 104 is in the closed position. Note that these are examples and the first roller 110 and the second roller 114 can be used to grasp an object (e.g., animate, inanimate, tissue, instrument, implantable) when the first roller 110 and the second roller 114 are in the closed position or in the open position or act (e.g., manipulate, dissect, isolate, separate, intervene, mount, drop, move, drag) with the object when the first roller 110 and the second roller 114 are in the closed position or in the open position. For example, the object when animate can include a tissue, an organ, a body part, whether of human or animal, or others. For example, the tissue can be a muscle tissue, a bone tissue, a nerve tissue, an organ tissue, or others. For example, the object when inanimate can include a medical device, a prosthesis, an implantable, a machine, a surgical instrument, or others. The closed position can be a clamping position.

A needle driver, as shown in FIGS. 1-31, which can include a needle or a thread, can be packaged, whether alone or with any other devices, whether disclosed herein or not, in a kit. For example, the kit can include a package (e.g., plastic bag, sealed bag, storage container, cardboard box, transport package, consumer package, bubble wrap, foam blanket, garment blanket, can, shrink-wrap, molded pulp, blister pack, box). For example, the package can include a cuboid box, a shipping box, an intermodal container, or others. The package can include one or more devices, as disclosed herein or not disclosed herein. The kit can include a set of instructions on a memory (e.g., mechanical memory, electronic memory, paper page, booklet, laminated card, flash drive, computer disc, website link). The set of instructions can instruct (e.g., text, graphics) a user on how to use a needle driver, as disclosed herein.

Features described with respect to certain embodiments may be combined in or with various some embodiments in any permutational or combinatory manner. Different aspects or elements of example embodiments, as disclosed herein, may be combined in a similar manner.

Although the terms first, second, can be used herein to describe various elements, components, regions, layers, or sections, these elements, components, regions, layers, or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Features described with respect to certain example embodiments can be combined and sub-combined in or with various other example embodiments. Also, different aspects or elements of example embodiments, as disclosed herein, can be combined and sub-combined in a similar manner as well. Further, some example embodiments, whether individually or collectively, can be components of a larger system, wherein other procedures can take precedence over or otherwise modify their application. Additionally, a number of steps can be required before, after, or concurrently with example embodiments, as disclosed herein. Note that any or all methods or processes, at least as disclosed herein, can be at least partially performed via at least one entity in any manner.

Example embodiments of this disclosure are described herein with reference to illustrations of idealized embodiments (and intermediate structures) of this disclosure. As such, variations from various illustrated shapes as a result, for example, of manufacturing techniques or tolerances, are to be expected. Thus, various example embodiments of this disclosure should not be construed as necessarily limited to various particular shapes of regions illustrated herein, but are to include deviations in shapes that result, for example, from manufacturing.

Any or all elements, as disclosed herein, can be formed from a same, structurally continuous piece, such as being unitary, or be separately manufactured or connected, such as being an assembly or modules. Any or all elements, as disclosed herein, can be manufactured via any manufacturing processes, whether additive manufacturing, subtractive manufacturing, or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Various corresponding structures, materials, acts, and equivalents of all means or step plus function elements in various claims below are intended to include any structure, material, or act for performing the function in combination with other claimed elements as specifically claimed. Various embodiments were chosen and described in order to best explain various principles of this disclosure and various practical applications thereof, and to enable others of ordinary skill in a pertinent art to understand this disclosure for various embodiments with various modifications as are suited to a particular use contemplated.

This detailed description has been presented for various purposes of illustration and description, but is not intended to be fully exhaustive or limited to this disclosure in various forms disclosed. Many modifications and variations in techniques and structures will be apparent to those of ordinary skill in an art without departing from a scope and spirit of this disclosure as set forth in various claims that follow. Accordingly, such modifications and variations are contemplated as being a part of this disclosure. Scope of this disclosure is defined by various claims, which include known equivalents and unforeseeable equivalents at a time of filing of this disclosure.

The invention claimed is:

1. A method comprising:
causing a device to be inserted into a first object, wherein the device includes a first jaw hosting a first shaft and a second jaw hosting a second shaft, wherein the first shaft hosts a first roller and a first set of teeth, wherein the second shaft hosts a second roller and a second set of teeth, wherein the second jaw moves relative to the first jaw between an open position and a closed position, wherein the first set of teeth meshes with the second set of teeth when the second jaw is in the closed position such that (a) the first set of teeth can drive the second set of teeth and (b) the first roller and the second roller can drive a needle therebetween when the first set of teeth drives the second set of teeth; and
causing the first roller and the second roller to at least one of grasp, manipulate, dissect, isolate, or separate a second object within the first object when the second jaw is in the closed position; and
coupling the first jaw to the second jaw when the second jaw is in the closed position via a mating mechanism located between the first shaft and the second shaft, wherein the mating mechanism includes a first retaining block supported by the first shaft and a second retaining block that opposes the first retaining block and is supported by the second shaft, and wherein the first retaining block is U-shaped and is configured to receive the second retaining block when the second jaw is in the closed position.

2. The method of claim 1, wherein the first roller includes a first groove portion, wherein the second roller includes a second groove portion, wherein the first groove portion faces the second groove portion when the second jaw is in the closed position, and
further comprising:
releasing the second object;
positioning the needle between the first groove portion and the second groove portion; and
driving the needle between the first groove portion and the second groove portion when the second jaw is in the closed position.

3. The method of claim 1, wherein the first jaw:
houses the first set of teeth, or
is self-aligning and the second jaw is self-aligning, or
has a longitudinal axis and wherein the first shaft rotates about the longitudinal axis, or
has a first longitudinal axis, wherein the first shaft rotates about the first longitudinal axis, and the second jaw has a second longitudinal axis, wherein the second shaft rotates about the second longitudinal axis, or
has a first longitudinal axis and the second jaw has a second longitudinal axis, wherein the first longitudinal axis is parallel to the second longitudinal axis, or houses the first set of teeth and wherein the second jaw houses the second set of teeth.

4. The method of claim 1, wherein the second jaw:

houses the second set of teeth, or is hingedly coupled to the first jaw such that the second jaw moves relative to the first jaw between the open position and the closed position, or is pivotally coupled to the first jaw such that the second jaw moves relative to the first jaw between the open position and the closed position, or has a longitudinal axis, wherein the second shaft rotates about the longitudinal axis, or is separate and distinct from the first jaw, or has a range of motion spanning between the closed position and the open position, or is biased open relative to the first jaw, or is biased closed relative to the first jaw, or is hingedly coupled to the first jaw without using a pin about which the second jaw moves relative to the first jaw between the open position and the closed position.

5. The method of claim 1, wherein the second jaw is biased open or biased closed relative to the first jaw.

6. The method of claim 1, wherein at least one of the first roller is diametrically larger than the first shaft or the second roller is diametrically larger than the second shaft.

7. The method of claim 1, wherein the closed position is a clamping position.

8. The method of claim 1, wherein the first set of teeth comprises a spur gear.

9. The method of claim 1, wherein the first set of teeth is exposed to the second jaw when the second jaw is in the open position.

10. The method of claim 1, wherein the second set of teeth is exposed to the first jaw when the second jaw is in the open position.

11. The method of claim 1, wherein the needle is recti-linear, non-rectilinear, or arcuate.

12. The method of claim 1, wherein the second jaw is in the closed position.

13. The method of claim 1, wherein the first retaining block defines an enclosed area.

14. The method of claim 1, wherein the closed position is a terminal position.

15. The method of claim 1, wherein the open position is a terminal position.

16. The method of claim 1, wherein the first roller and the first set of teeth are spaced apart from each other on the first shaft.

17. The method of claim 1, wherein the second roller and the second set of teeth are spaced apart from each other on the second shaft.

18. The method of claim 1, wherein the first jaw is self-aligning and the second jaw is self-aligning.

19. The method of claim 1, further comprising:

pulling the second jaw from the closed position to the open position using a line coupled to the second jaw, or extending a line along a lateral channel in the first jaw before extending the line over the second jaw, or clamping a tissue between the first roller and the second roller when the second jaw is in the closed position, or causing the second jaw to move between the closed position and the open position based on a bar supported via the first jaw being moved along the first jaw, or causing the second jaw to move from the closed position to the open position based on a bar supported via the first jaw being moved away from the first set of teeth, or counting how many times the first jaw and the second jaw have concurrently undergone a sterilization procedure, using a counter, or driving the first shaft with a third shaft coupled to the first shaft and supported by the first jaw, and causing the second jaw to move from the closed position to the open position based on a bar supported via the first jaw being moved away from the first set of teeth along the third shaft, or moving the second jaw relative to the first jaw between the open position and the closed position by pivotally mating a female portion and a male portion, wherein the first jaw includes the female portion and the first set of teeth is positioned between the first roller and the female portion, and wherein the second jaw includes the male portion and the second set of teeth is posi-tioned between the second roller and male portion, or pushing the second jaw from the open position to the closed position using a line coupled to the second jaw, or supporting at least one of the first jaw, the second jaw, or the first jaw and the second jaw, using an end effector, or hosting the first jaw and the second jaw using a housing, or rotating the first shaft using a knob coupled to the first shaft, or driving the first jaw via a first lever, and moving the second jaw relative to the first jaw between the open position and the closed position using a second lever, wherein the device further comprises a tube configured to support the first jaw and the second jaw; and a housing configured to support a handle, the first lever, and the second lever, wherein the tube extends from the housing such that the first jaw and the second jaw are distal to the housing, wherein the first lever is movable relative to the handle, and wherein the second lever is movable relative to the handle, or positioning the second set of teeth between the second roller and a collar that extends about the second shaft, or driving the first shaft using a third shaft that is configured to at least one of receive the first shaft or extend into the first shaft, wherein the first jaw supports the third shaft, or counting how many times at least one of the first shaft has been rotated, the second shaft has been rotated, or the second jaw has moved relative to the first jaw, using a counter, or counting how many times a lever coupled to at least one of the first jaw or the second jaw has been pulled, using a counter, or engaging a gear wheel in which the first set of teeth is mounted onto the first shaft.

20. The method of claim 19, wherein the pulling the second jaw from the closed position to the open position using a line coupled to the second jaw, or the extending a line along a lateral channel in the first jaw before extending the line over the second jaw, or the pushing the second jaw from the open position to the closed position using a line coupled to the second jaw, further comprises the first set of teeth extending between the first roller and the line.

21. The method of claim 19, wherein the second shaft includes an end portion on which the second roller is mounted.

22. The method of claim 1, wherein the second shaft is rotationally constrained or unconstrained in the open position.

23. The method of claim 22, wherein the first shaft is parallel to the second shaft external to the first jaw.

* * * * *